(12) United States Patent
O'Neill et al.

(10) Patent No.: US 9,492,456 B2
(45) Date of Patent: Nov. 15, 2016

(54) VALOMACICLOVIR POLYMORPHS

(71) Applicant: EPIPHANY BIOSCIENCES, INC., San Francisco, CA (US)

(72) Inventors: Mike H. O'Neill, Concord, OH (US); Gregory P. Butke, Concord, OH (US)

(73) Assignee: EPIPHANY BIOSCIENCES, INC., San Francisco, CA (US)

( * ) Notice: Subject to any disclaimer, the term of this patent is extended or adjusted under 35 U.S.C. 154(b) by 0 days.

(21) Appl. No.: 14/309,580

(22) Filed: Jun. 19, 2014

(65) Prior Publication Data

US 2015/0051229 A1 Feb. 19, 2015

Related U.S. Application Data

(63) Continuation of application No. 13/778,282, filed on Feb. 27, 2013, now abandoned, which is a continuation of application No. 12/676,361, filed as application No. PCT/US2008/010937 on Sep. 18, 2008, now abandoned.

(60) Provisional application No. 60/994,719, filed on Sep. 21, 2007.

(51) Int. Cl.
  *C07D 473/18* (2006.01)
  *A61K 31/522* (2006.01)
  *C07D 473/04* (2006.01)

(52) U.S. Cl.
  CPC ........... *A61K 31/522* (2013.01); *C07D 473/04* (2013.01); *C07D 473/18* (2013.01); *C07B 2200/13* (2013.01)

(58) Field of Classification Search
  CPC .................... C07D 473/18; A61K 31/522
  See application file for complete search history.

(56) References Cited

U.S. PATENT DOCUMENTS

| 6,184,376 B1 | 2/2001 | Leanna et al. |
| 6,255,312 B1 | 7/2001 | Engelhardt et al. |
| 6,407,241 B1 | 6/2002 | Jensen et al. |
| 7,189,849 B2 | 3/2007 | Leanna et al. |
| 2004/0147743 A1 | 7/2004 | Jansen et al. |
| 2005/0085476 A1 | 4/2005 | Seko et al. |
| 2006/0264428 A1 | 11/2006 | Takahashi et al. |

FOREIGN PATENT DOCUMENTS

| EP | 0593976 A1 | 4/1994 |
| JP | S5245716 B1 | 11/1977 |
| JP | S61263985 A | 11/1986 |
| JP | H04235188 A | 8/1992 |
| JP | H0753581 A | 2/1995 |
| JP | H11139975 A | 5/1999 |
| JP | 2003073353 A | 3/2003 |
| JP | 2004149451 A | 5/2004 |
| WO | 9703959 A1 | 2/1997 |
| WO | 9834917 A2 | 8/1998 |
| WO | 0008025 A1 | 2/2000 |
| WO | 03002564 | 1/2003 |

OTHER PUBLICATIONS

Lamarre, Daniel. Nature. 426 (2003) 186-189.*
Littler, Eddy. Antiviral Chemistry & Chemotherapy (2005) 16:155-168.*
Clercq, Erik. British Journal of Pharmacology (2006) 147 1-11.*
Hambleton, Sophie. Clinical Mocrobiology Reviews (2005) 70-80.*
S.L. Morissette et al., "High-Throughput Crystallization: Polymorphs, Salts, Co-Crystals and Solvates of Pharmaceutical Solids," Adv. Drug Deliv. Rev. 56: 275-300 (2004).
"Additives for Crystallization" (http://www.chem.gla.ac.uk/research/groups/protein/mirror/stura/cryst/add.html), Sep. 23, 1997.
"Genital Herpes Treatment Center: Treatment Options for Genital Herpes," http://www.webmd.com/genital-herpes/guide/genital-herpes-treatment-options, Aug. 6, 2012.
International Search Report on the corresponding PCT application, PCT Application Serial No. PCT/US2008/010937, mailed Dec. 1, 2008.
Byrn et al., "Pharmaceutical Solids: A Strategic Approach to Regulatory Considerations", Pharmaceutical Research, Jul. 1995, vol. 12, No. 7, pp. 945-954.
Bavin, "Polymorphism in Process Development", Chemistry & Industry, vol. 21, Aug. 21, 1989, pp. 527-529.

* cited by examiner

*Primary Examiner* — Golam M M Shameem
*Assistant Examiner* — Laura Daniel
(74) *Attorney, Agent, or Firm* — Ditthavong & Steiner, P.C.

(57) ABSTRACT

The present invention relates to crystalline forms of valomaciclovir, processes for preparing crystalline forms of valomaciclovir, pharmaceutical compositions thereof and methods of using thereof.

13 Claims, 30 Drawing Sheets

*Structure drawings of valomaciclovir (A) and H2G (B)*

EPB-348

C₃₃H₅₈N₆O₅
Mol. Wt.: 618.85

H2G

*X-ray diffraction characteristcs of valomaciclovir Polymorph A*

*Valomaciclovir synthesis: Steps 1-5*

*Valomaciclovir synthesis: Steps 6-12*

*Variations of final steps in preparation of valomaciclovir*

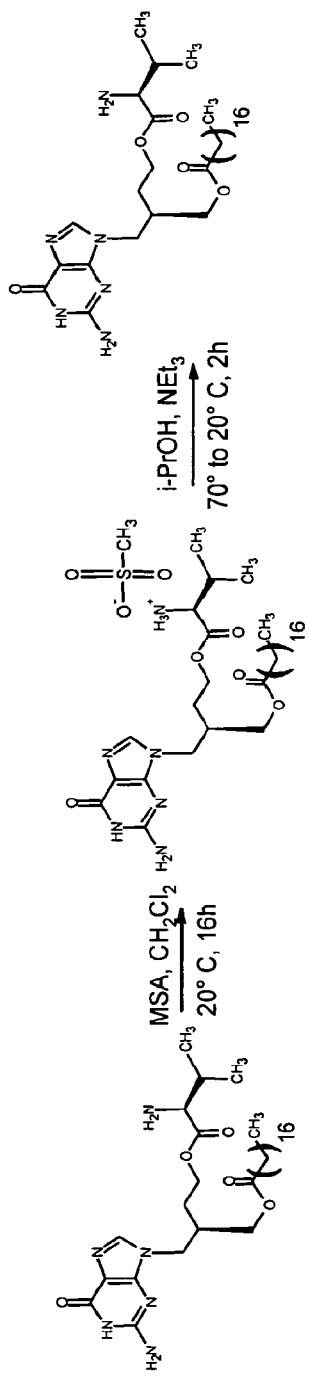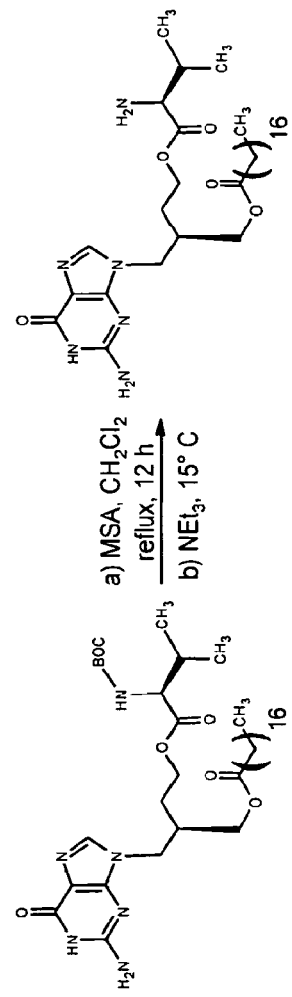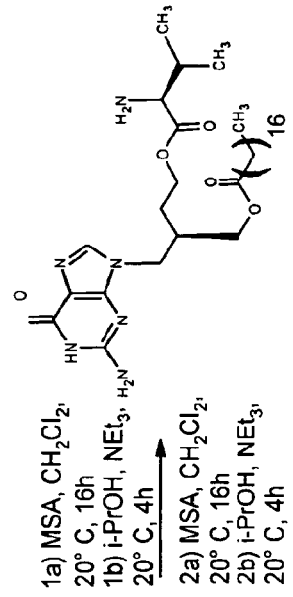
Fig. 5C
Fig. 5D

*Polymorph Screening Recrystallization Panel 1*

| Well | Solvent | Approximate Solubility mg/mL | Recrystallized solids | XRD Group |
|---|---|---|---|---|
| 1 | methanol | <3.3 | white solids | ? |
| 2 | ethanol | <3.3 | light yllw solids | B4 |
| 3 | trifluoroethanol | >50 | white gel | C |
| 4 | 2 propanol | <3.1 | sm wh solids | B1 |
| 5 | sec-butanol | <3.3 | sm wh solids | C |
| 6 | 1 propanol | <3.3 | sm wh solids | B1 |
| 7 | 1 butanol | ~3.3 | white solids | B2 |
| 8 | water | <3.3 | ~ no sample | - |
| 9 | DMF | >12.5 | white powder | A |
| 10 | DMA | >16.7 | tacky white gel | - |
| 11 | pyridine | >25 | white powder | A |
| 12 | nitromethane | <3.3 | sm yllw residue | - |
| 13 | acetone | ~3.3 | off white solids | C |
| 14 | MEK | <3.3 | dark yllw/orange solid | - |
| 15 | isopropyl ether | <3.3 | v sm wh/yllw film | - |
| 16 | EtOAc | <3.3 | v sm yllw glass | - |
| 17 | MTBE | <3.3 | v sm yllw glass | - |
| 18 | isopropyl acetate | <3.3 | v sm off white film | - |
| 19 | THF | >25 | clear glass | - |
| 20 | acetonitrile | <3.3 | sm yllw glass | - |
| 21 | methylene chloride | >50 | white dry gel | B3 |
| 22 | chloroform | >50 | white gel | B3 |
| 23 | toluene | <5.6 | sm lt yllw solid | - |
| 24 | heptane | <3.3 | sm yllw glass | - |
| 25 | petroleum ether | <3.3 | v sm yllw glass | - |
| 26 | t butanol | <3.3 | white solids | B2 |

Fig. 10A

*Polymorph Screening Recrystallization Panel 2*

| Solvent Matrix and XRD Result for Recrystallization Panel 2 ||||||
|---|---|---|---|---|---|
| Solvent | | 1 | 2 | 3 | Co/AntiSolvent |
| MeCl2 | A | 12:3 | 7.5:7.5 | 3:12 | 2-propanol |
| EtOH | B | 12:3 | 7.5:7.5 | 3:12 | water |
| Acetone | C | 12:3 | 7.5:7.5 | 3:12 | 1-propanol |
| Acetonitrile | D | 12:3 | 7.5:7.5 | 3:12 | ethyl acetate |
| Trifluoroethanol | E | 12:3 | 7.5:7.5 | 3:12 | THF |
| DMF | F | 12:3 | 7.5:7.5 | 3:12 | acetonitrile |
| MeOH | G | 12:3 | 7.5:7.5 | 3:12 | chloroform |
| EtOH | H | 12:3 | 7.5:7.5 | 3:12 | toluene |
| Solvent | | 1 | 2 | 3 | Co/AntiSolvent |
| MeCl2 | A | C | C | C | 2-propanol |
| EtOH | B | F | - | - | water |
| Acetone | C | B2 | B2 | B2 | 1-propanol |
| Acetonitrile | D | - | B2 | A | ethyl acetate |
| Trifluoroethanol | E | - | - | - | THF |
| DMF | F | C | B2 | B2 | acetonitrile |
| MeOH | G | B3 | B3 | B4 | chloroform |
| EtOH | H | B4 | C | C | toluene |

Fig. 10B

*Polymorph Screening Recrystallization Panel 3*

| Solvent Matrix and XRD Result for Recrystallization Panel 3 | | | | | |
|---|---|---|---|---|---|
| Solvent | | 1 | 2 | 3 | Co/AntiSolvent |
| MeCl2 | A | 12:3 | 7.5:7.5 | 3:12 | 2-propanol |
| EtOH | B | 12:3 | 7.5:7.5 | 3:12 | water |
| Acetone | C | 12:3 | 7.5:7.5 | 3:12 | 1-propanol |
| Acetonitrile | D | 12:3 | 7.5:7.5 | 3:12 | ethyl acetate |
| Trifluoroethanol | E | 12:3 | 7.5:7.5 | 3:12 | THF |
| DMF | F | 12:3 | 7.5:7.5 | 3:12 | acetonitrile |
| MeOH | G | 12:3 | 7.5:7.5 | 3:12 | chloroform |
| EtOH | H | 12:3 | 7.5:7.5 | 3:12 | toluene |
| Solvent | | 1 | 2 | 3 | Co/AntiSolvent |
| MeCl2 | A | C | C | C | 2-propanol |
| EtOH | B | F | C | C | water |
| Acetone | C | - | C | C | 1-propanol |
| Acetonitrile | D | - | B2 | B2 | ethyl acetate |
| Trifluoroethanol | E | - | - | - | THF |
| DMF | F | A | B2 | B2 | acetonitrile |
| MeOH | G | C | C | C | chloroform |
| EtOH | H | C | C | C | toluene |

Fig. 10C

*Polymorph Screening Recrystallization Panel 4*

| Solvent Matrix and XRD Result for Recrystallization Panel 4 ||||||
|---|---|---|---|---|---|
| Solvent | | 1 | 2 | 3 | Co/AntiSolvent |
| MeCl2 | A | 12:3 | 7.5:7.5 | 3:12 | 2-propanol |
| EtOH | B | 12:3 | 7.5:7.5 | 3:12 | 2-propanol |
| Acetone | C | 12:3 | 7.5:7.5 | 3:12 | 1-propanol |
| Acetonitrile | D | 12:3 | 7.5:7.5 | 3:12 | ethyl acetate |
| Trifluoroethanol | E | 12:3 | 7.5:7.5 | 3:12 | THF |
| DMF | F | 12:3 | 7.5:7.5 | 3:12 | acetonitrile |
| EtOH | G | 12:3 | 7.5:7.5 | 3:12 | MeOH |
| EtOH | H | 12:3 | 7.5:7.5 | 3:12 | toluene |

| Solvent | | 1 | 2 | 3 | Co/AntiSolvent |
|---|---|---|---|---|---|
| MeCl2 | A | C | B2 | B2 | 2-propanol |
| EtOH | B | B1 | A | B2 | 2-propanol |
| Acetone | C | C | B2 | C | 1-propanol |
| Acetonitrile | D | B2 | B2 | B2 | ethyl acetate |
| Trifluoroethanol | E | - | - | - | THF |
| DMF | F | B2 | B2 | B2 | acetonitrile |
| EtOH | G | B2 | B2 | B4 | MeOH |
| EtOH | H | B2 | C | C | toluene |

Fig. 10D

*Variable Temperature Characteristics of Form B1 (Lot 12-03-011)*

*Group B3-Diffraction and Thermal Characteristics*

*Group B3-Cyclic Thermal Characteristics*

*Group C-Diffraction Characteristics*

VALOMACICLOVIR POLYMORPHS

CROSS-REFERENCE TO RELATED APPLICATIONS

This application is a continuation of U.S. application Ser. No. 13/778,782 filed Feb. 27, 2013, which in turn is a continuation of U.S. application Ser. No. 12/676,361 filed Mar. 4, 2010, which is a United States National Phase of PCT/US2008/010937 filed Sep. 18, 2008 which claims priority from U.S. Provisional Application No. 60/994,719 filed on Sep. 21, 2007, each of which is incorporated herein by reference in its entirety.

FIELD OF THE INVENTION

The present invention relates to crystalline forms of valomaciclovir, processes for preparing crystalline forms of valomaciclovir, pharmaceutical compositions thereof and methods of using thereof.

BACKGROUND OF THE INVENTION

The ability of a compound to exist in different crystal structures is known as polymorphism. These different crystalline forms are known as "polymorphic modifications" or "polymorphs." While polymorphs have the same chemical composition, they differ in packing and geometrical arrangement and exhibit different physical properties such as melting point, shape, color, density, hardness, deformability, stability, dissolution and the like (Theory and Origin of Polymorphism in "Polymorphism in Pharmaceutical Solids" (1999) ISBN: 0-8247-0237).

Valomaciclovir [L-valine, (3R)-3-[(2-amino-1,6-dihydro-6-oxo-9H-purin-9-yl)methyl]-4-[(1-oxooctadecyl)oxy]butyl ester], also known by the USAN as valomaciclovir stearate or the proprietary codes EPB-348, MIV-606 or RP-606 (FIG. 1A), is the diester prodrug (valine and stearic acid) of the acyclic guanosine derivative H2G (FIG. 1B), a potent, broad-spectrum anti-herpes agent. H2G has potent activity against human varicella zoster virus (VZV), Epstein-Barr virus (EBV), human herpesvirus-6 (HHV-6), HSV-I, and HSV-2. U.S. Pat. No. 5,869,493 describes the preparation and activity of valomaciclovir.

Valomaciclovir has been under development as an orally active agent against shingles (zoster) and other viral diseases. Valomaciclovir was safe and well tolerated after multiple dosing with total daily doses of up to 6.0 g as shown in several phase I human clinical studies. Results from a phase II study (M98-829) using a suspension of valomaciclovir at 250, 500, and 750 mg administered BID for 7 days to zoster patients, with acyclovir as a control, provided proof-of-concept for zoster lesion healing and a basis for further use of valomaciclovir in patients with post-herpetic neuralgia.

Valomaciclovir includes a guanine moiety, an amino acid ester and a long chain fatty acid ester. Each of these components has been associated with various formulation difficulties, and valomaciclovir is no exception. Published patent applications (e.g., International Publications Nos. WO98/34917, WO00/08025 and WO03/02564) and U.S. Pat. No. 6,184,376 describe various synthetic routes for valomaciclovir. However, these prior art synthetic routes tended to produce amorphous materials, mixtures of amorphous and crystalline material or mixtures of poorly characterized partially ordered materials. The resulting material often suffered from extremely poor flowability and agglomeration, significantly hampering handling and processing. Previous phase I and phase II clinical trials with valomaciclovir employed liquid suspensions that avoided the difficulties in handling and processing because of the physical nature of the material. However, liquid suspensions are not a clinically preferred formulation, because they are not easy to administer, especially to elderly patients who are the main patient population for a shingles medication.

Accordingly, there remains a need for stable crystalline forms of valomaciclovir and reproducible processes for producing these stable forms.

SUMMARY OF THE INVENTION

The current invention satisfies these and other need by providing, in a first aspect, stable crystalline forms of valomaciclovir, including Polymorph A enriched valomaciclovir. Polymorph A is both the most crystalline and thermodynamically the most stable polymorph of valomaciclovir.

In a second aspect, a pharmaceutical composition comprising stable crystalline forms of valomaciclovir and a pharmaceutically compatible carrier or diluent is provided.

In a third aspect, there is provided a reproducible process of preparing stable crystalline forms of valomaciclovir. The process comprises dissolving valomaciclovir in a lower alkanol solvent or a mixed solvent of lower alkanols by heating to an appropriate internal temperature, cooling with stirring to effect substantial crystallization of valomaciclovir, and collecting the crystalline product.

In a fourth aspect, the present invention provides a method of treating a viral infection in a patient comprising administering to the subject a therapeutically effective amount of a stable crystalline form of valomaciclovir or a pharmaceutical composition thereof. The viral infections treatable using the method of this invention are caused by, for example and without limitation, varicella zoster virus, herpes simplex viruses (HSV-1 and HSV-2), human herpes viruses (HHV-6, HHV-7 and HHV-8), Epstein Barr virus, cytomegalovirus, and HIV.

BRIEF DESCRIPTION OF THE DRAWINGS

FIG. 5A, FIG. 5B, FIG. 5C, and FIG. 5D show variations of final steps in the preparation of valomaciclovir.

FIG. 10A, FIG. 10B, FIG. 10C, and FIG. 10D show recrystallization panels in polymorph screening studies.

DETAILED DESCRIPTION

Figure 1A:
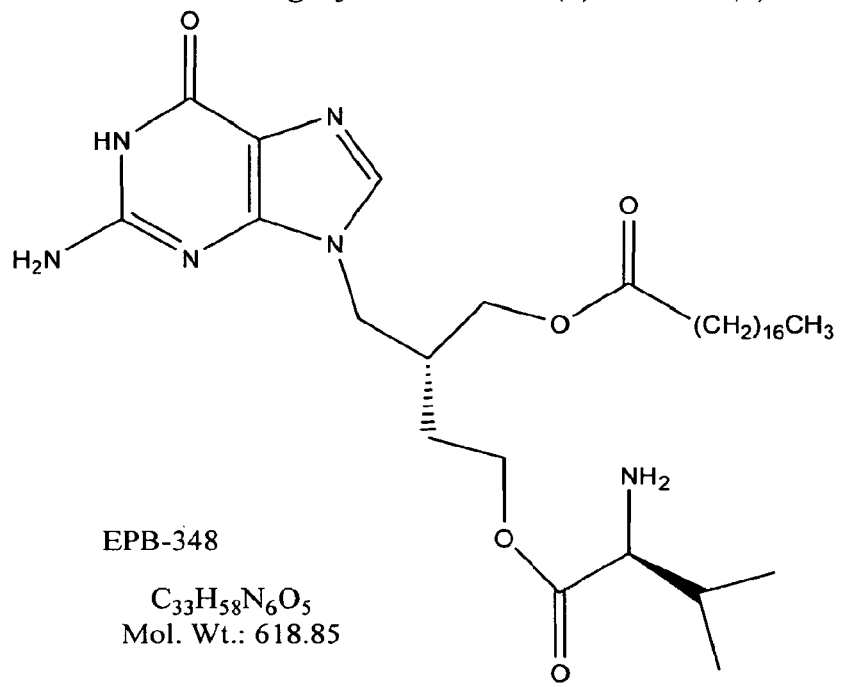
FIG. 1 shows the structure of valomaciclovir (FIG. 1A) and H2G (FIG. 1B).

The description may be better appreciated in view of the following definitions and explanatory comments.

Other than in the operating examples, or where otherwise indicated, all numbers expressing quantities of ingredients, reaction conditions, and so forth used in the specification and claims are to be understood as being modified in all instances by the term "about".

Throughout this specification, the word "comprise," or variations such as "comprises" or "comprising," will be understood to imply the inclusion of a stated element, integer or step, or group of elements, integers or steps, but not the exclusion of any other element, integer or step, or group of elements, integers or steps.

"Pharmaceutically acceptable salt" refers to a salt of valomaciclovir which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Pharmaceutically acceptable vehicle" refers to a diluent, adjuvant, excipient or carrier with which valomaciclovir is administered.

The terms "subject", "individual" or "patient" are used interchangeably herein and refer to a vertebrate, preferably a mammal. Mammals include, but are not limited to, murines, rodents, simians, humans, farm animals, sport animals and pets.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Treating" or "treatment" of any disease or disorder refers, in some embodiments, to ameliorating the disease or disorder (i.e., arresting or reducing the development of the disease or at least one of the clinical symptoms thereof). In other embodiments "treating" or "treatment" refers to ameliorating at least one physical parameter, which may not be discernible by the patient. In yet other embodiments, "treating" or "treatment" refers to inhibiting the disease or disorder, either physically (e.g., stabilization of a discernible symptom), physiologically, (e.g., stabilization of a physical parameter) or both. In yet other embodiments, "treating" or "treatment" refers to delaying the onset or progression of the disease or disorder.

"Therapeutically effective amount" means the amount of valomaciclovir that, when administered to a patient for treating a disease, is sufficient to effect such treatment for the disease. The "therapeutically effective amount" can vary depending on the disease and its severity and the age, weight, etc., of the patient to be treated.

Polymorph screening studies of valomaciclovir revealed several different forms, including but not limited to Forms A, B1, B2, B3, B4, C, and H. Each group has different diffraction characteristics as well as different thermal features.

Valomaciclovir polymorphs can be characterized using analytical methods including, without limitation, differential scanning calorimetry (DSC), polarized light hot-stage microscopy (HSM), thermogravimetric analysis (TGA), Fourier transform infrared spectroscopy (FTIR), Fourier transform nuclear magnetic resonance (NMR) spectroscopy, variable temperature powder X-ray diffraction (XRD) and high performance liquid chromatography (HPLC).

Figure 1B:
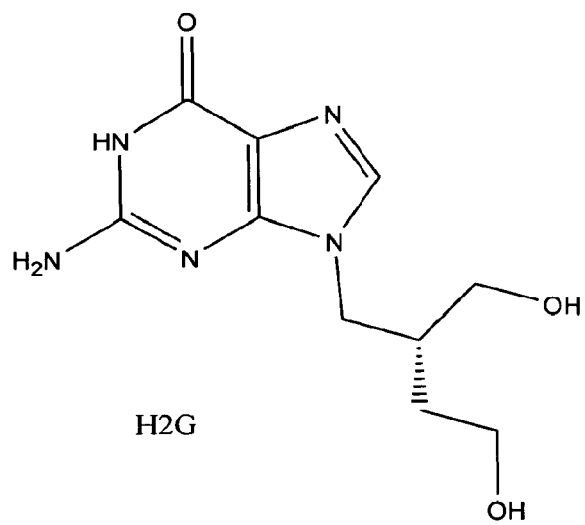
Figure 2:
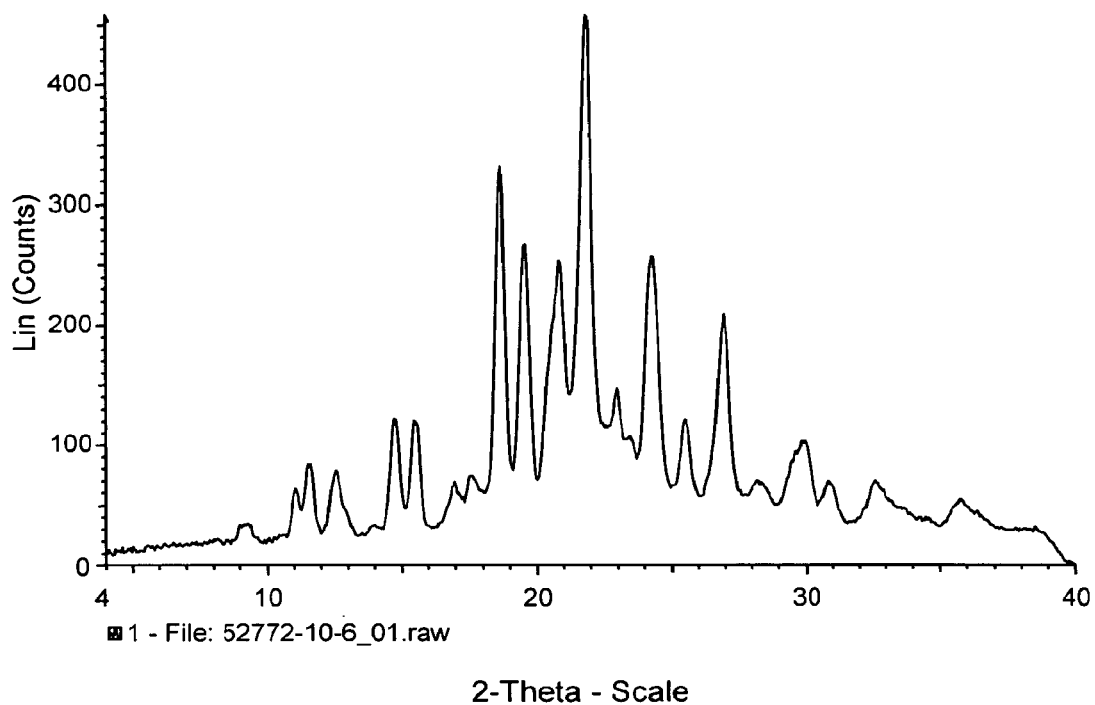
FIG. 2 shows the characteristic X-ray diffraction patterns of valomaciclovir Polymorph A.
Figure 3:
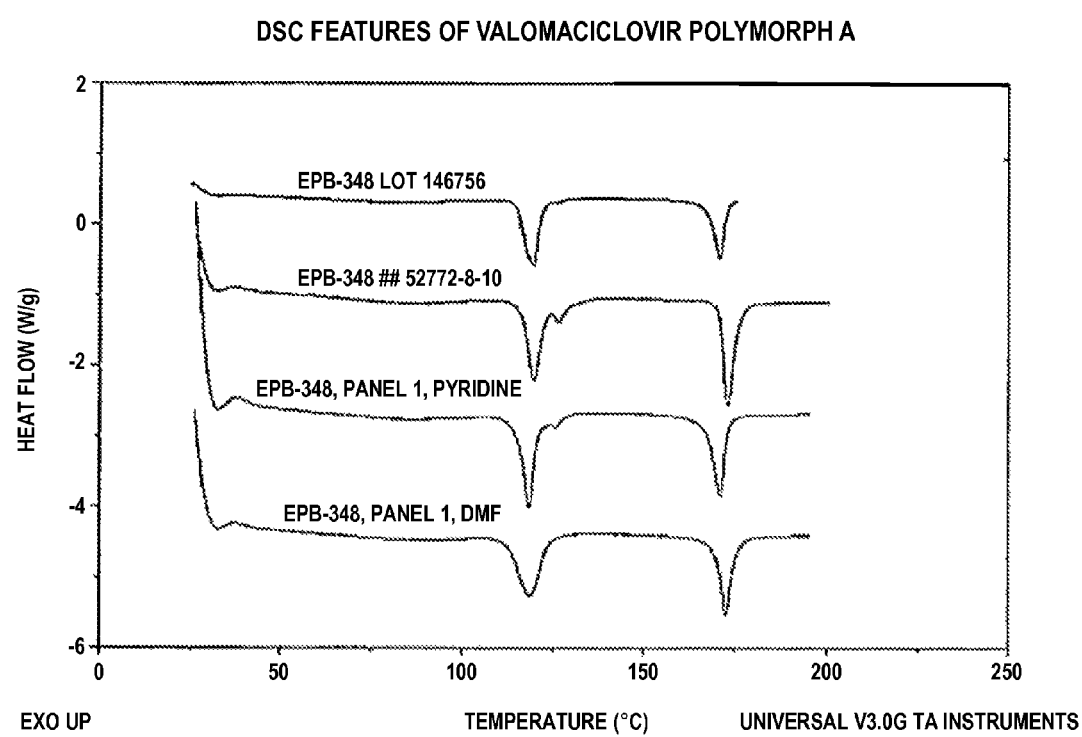
FIG. 3 shows the characteristic DSC thermogram of valomaciclovir Polymorph A.
Figure 4A:
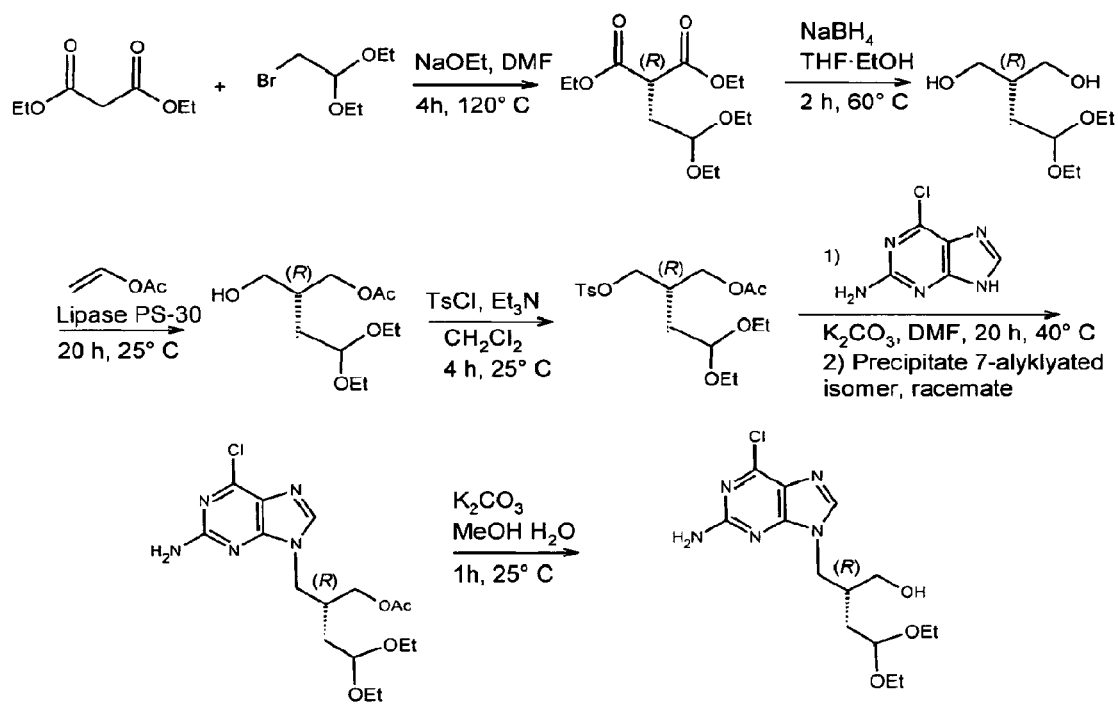
FIGS. 4A and 4B show a synthetic route for the preparation of valomaciclovir.
Figure 4B:
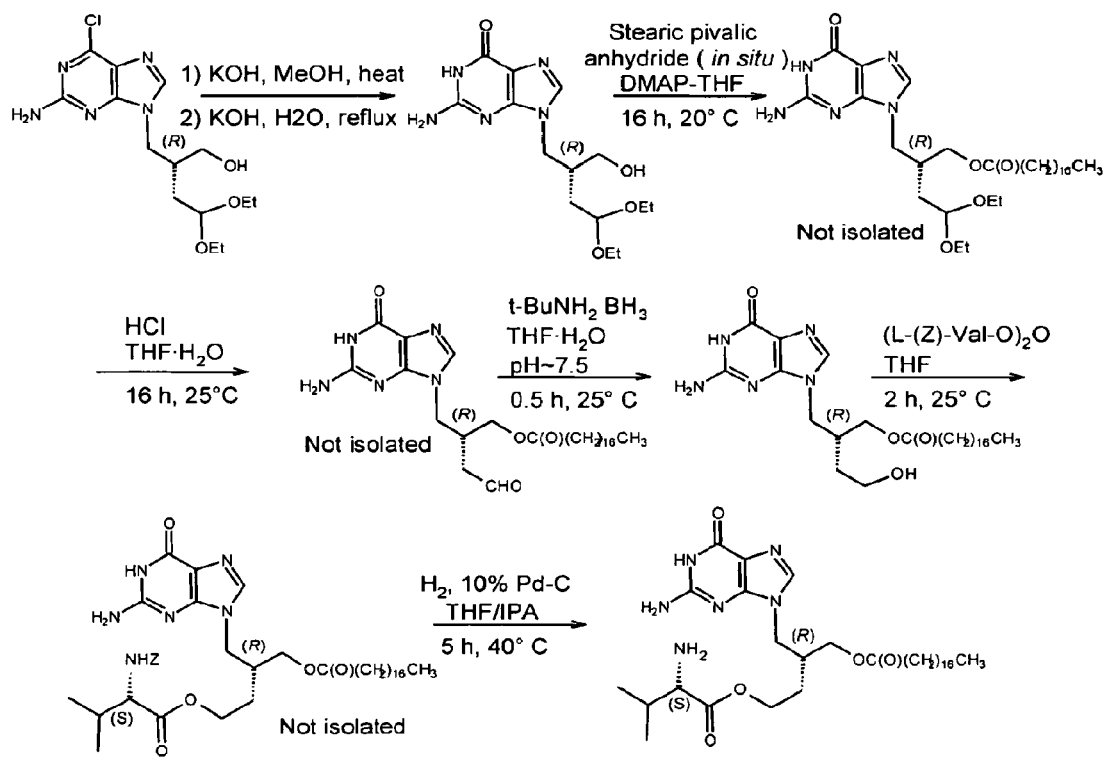

FIG. 1A shows the structure of EPB-348 and FIG. 1B shows the structure of H2G. A characteristic X-ray diffraction data of Form A is shown in Table 1, the diffraction patterns are shown in FIG. 2; and a characteristic differential scanning calorimeter thermogram is shown in FIG. 3. Table 1 lists some of the peaks found in the XRD spectrum. Other peaks with lower intensities may also be present. FIG. 4A shows initial steps in the synthesis of valomaciclovir stearate. FIG. 4B shows subsequent steps in the synthesis of valomaciclovir stearate.

The characteristic DSC features of Polymorph A include an endotherm from about 105° C. to about 125° C., and centered near 115° C. (typically 20-30 J/g) and a melting endotherm from about 170° C. to about 180° C., and centered near 171° C. (typically around 20-30 J/g). Some samples showed additional small signals (approximately 6 J/g).

TABLE 1

Characteristic peak listing of Polymorph
A X-ray powder diffraction patterns

| 2-Theta Angle (°) | d value (Ångstrom) |
|---|---|
| 14.7 | 6.01 |
| 15.5 | 5.72 |
| 18.6 | 4.76 |
| 19.5 | 4.54 |
| 20.8 | 4.26 |
| 21.8 | 4.07 |
| 22.9 | 3.87 |
| 24.3 | 3.66 |
| 25.5 | 3.49 |
| 27.0 | 3.31 |
| 29.9 | 2.98 |

It will be appreciated that the exact diffraction and thermal characteristics vary slightly depending on the type of instrument and analytical conditions employed. For example, instruments used for X-ray diffraction pattern typically have an ±0.2 error for the measured 2-theta angles.

Polymorph A" according to this invention is a crystalline form of valomaciclovir having substantially the same X-ray diffraction pattern as shown in Table 1 or FIG. 2, or having substantially the same DSC thermograms as shown in FIG. 3. In some embodiments, Polymorph A enriched valomaciclovir contains at least about 90% Polymorph A. In other embodiments, Polymorph A enriched valomaciclovir contains at least about 95% Polymorph A. In yet other embodiments, Polymorph A enriched valomaciclovir contains at least about 99% Polymorph A.

The Polymorph A content or the polymorphic purity of the polymorphs described herein may be determined by methods known in the art, including, but not limited to, X-ray diffraction (XRD), differential scanning calorimetry (DSC), polarized light hot-stage microscopy (HSM), thermogravimetric analysis (TGA), Fourier transform infrared spectroscopy (FTIR) and variable temperature powder XRD.

Also provided herein is a reproducible process of preparing high quality valomaciclovir enriched in Polymorph A. The process comprises dissolving valomaciclovir in a lower alkanol solvent or a mixed solvent of lower alkanols by heating to an appropriate internal temperature, cooling with stirring to effect substantial crystallization of valomaciclovir and collecting the crystalline product.

FIG. 5A, FIG. 5B, FIG. 5C, and FIG. 5D show variations of final steps in the preparation of valomaciclovir stearate. A batch of valomaciclovir (Lot 45-548-YS-00) prepared according to the scheme shown in FIG. 5A was purified as following: the crude product was dissolved in CH$_2$Cl$_2$, the solution was washed with water, and the CH$_2$Cl$_2$ removed in vacuo. The residue was dissolved in i-PrOH and the product precipitated with isopropyl acetate. The precipitate was filtered, dried and oscillated over a 10 mesh screen.

Figure 5A:
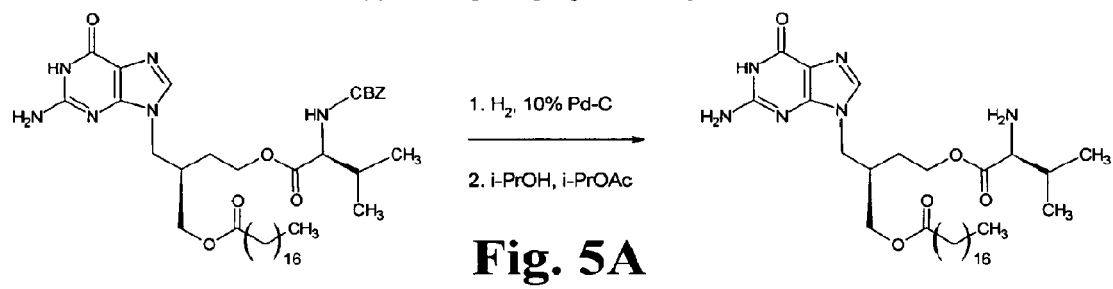
Figure 5B:
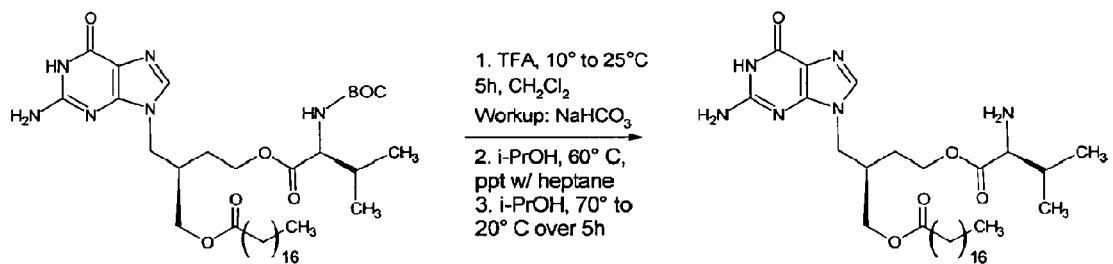

Another batch of valomaciclovir (Lot 12-03-011) was prepared according to the scheme shown in FIG. 5B and was purified as following: the crude product was dissolved in i-PrOH, heated to 70° C., and the hot solution was filtered and cooled to 20° C. over 5 hours. The product was collected, washed with i-PrOH and dried under vacuum at 45° C. for 15 h.

Another batch of valomaciclovir (Lot 12-03-018) was prepared according to the scheme shown in FIG. 5C. The final steps of synthesis and purification involve the following: the mesylate salt was dissolved in i-PrOH, NEt$_3$ was added, and the mixture heated to 70° C. The hot solution was cooled to 20° C. over 4 h and agitated at 20° C. for at least 2 h. The crystalline product was filtered, washed with i-PrOH, and vacuum dried.

Two other batches of valomaciclovir (Lot 146756 and Lot 06-01159-2) were prepared according a process in which the CBZ protecting group was replaced with the Boc protecting group (FIG. 5D). The final purification steps of Lot 146756 involve two iterations of the following steps: crude EPB-348 free base was dissolved in CH$_2$Cl with heating, and methanesulfonic acid was added, and the solution cooled to 20° C., stirred for 16 h, filtered, and dried. The residue was dissolved in i-PrOH and NEt$_3$ was added. The mixture was heated to dissolve all solids, cooled to 20° C., stirred for 4 h, filtered, and dried. The final steps in purification of Lot 06-01159-2 involve two iterations of the following steps: crude EPB-348 free base was dissolved in CH$_2$Cl$_2$ and heated to 35° C. Methanesulfonic acid was added, the solution cooled to 20° C., stirred for 16 h, filtered, and dried. The residue was dissolved in i-PrOH, NEt$_3$ was added, and the solution was heated to 70° C., cooled to 20° C., stirred for 2 h, filtered, and dried.

Figure 5E:
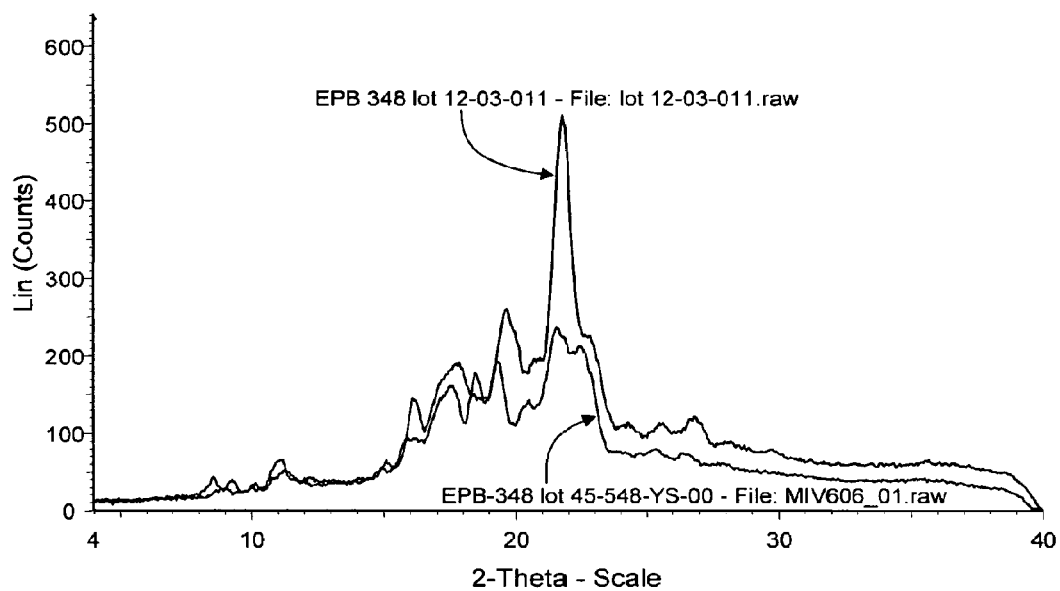
FIG. 5E shows the powder XRD patterns of samples lots 45-548-YS-00 and 12-03-011.
Figure 5F:
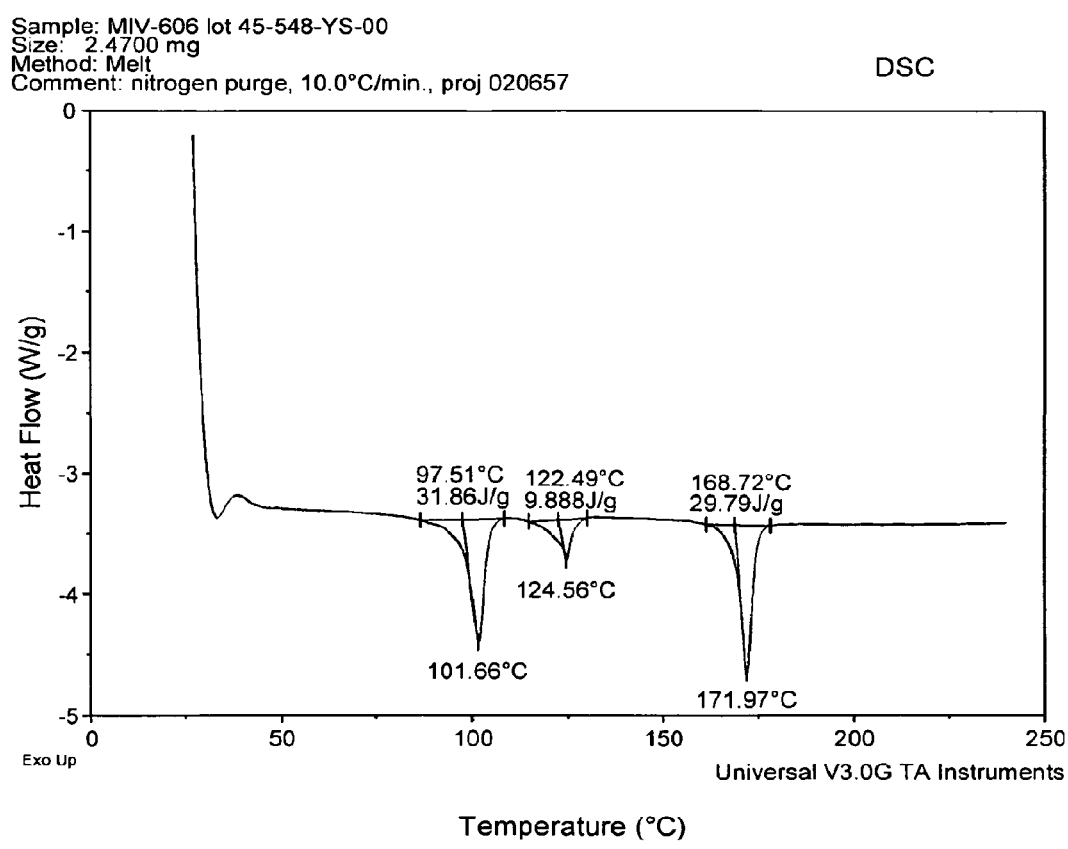
FIG. 5F shows the DSC plots of samples lots 45-548-YS-00.
Figure 5G:
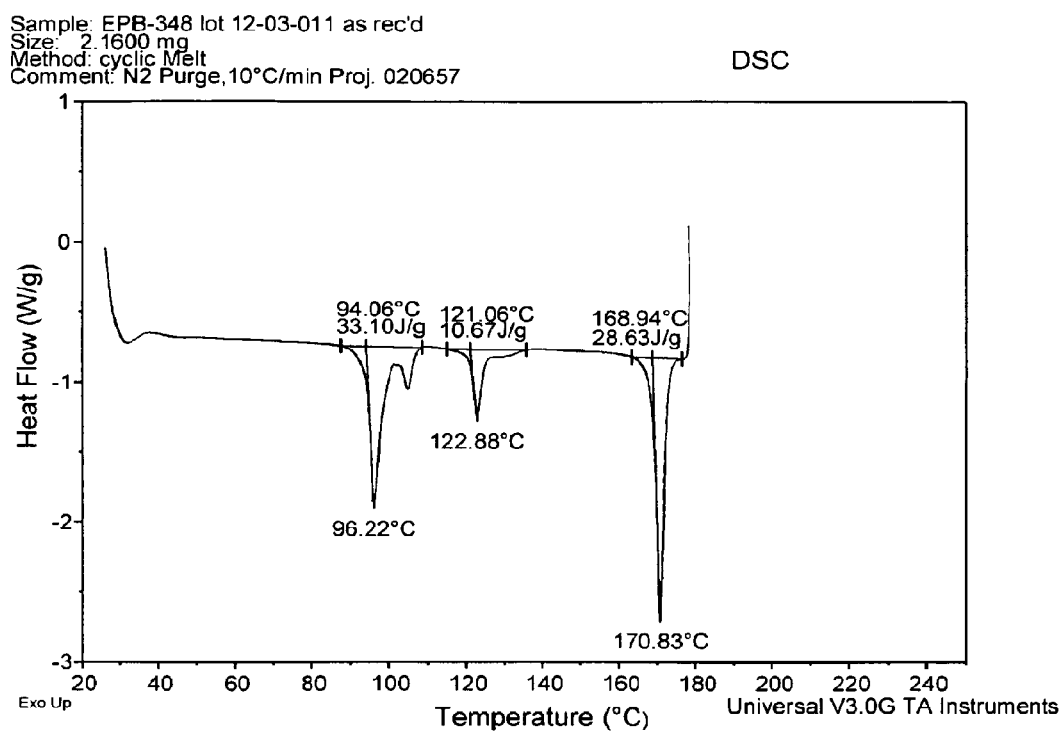
FIG. 5G shows the DSC plots of samples lots 2-03-011H.

XRD and DSC analysis of these batches revealed different polymorphic forms. As shown in FIGS. 5E, 5F and 5G, the powder XRD patterns and DSC thermograms observed for Lot 45-548-YS-00 and Lot 12-03-011 are distinctively different from those of Polymorph A. They are identified as Forms B2 and B1, respectively.

Figure 5H:
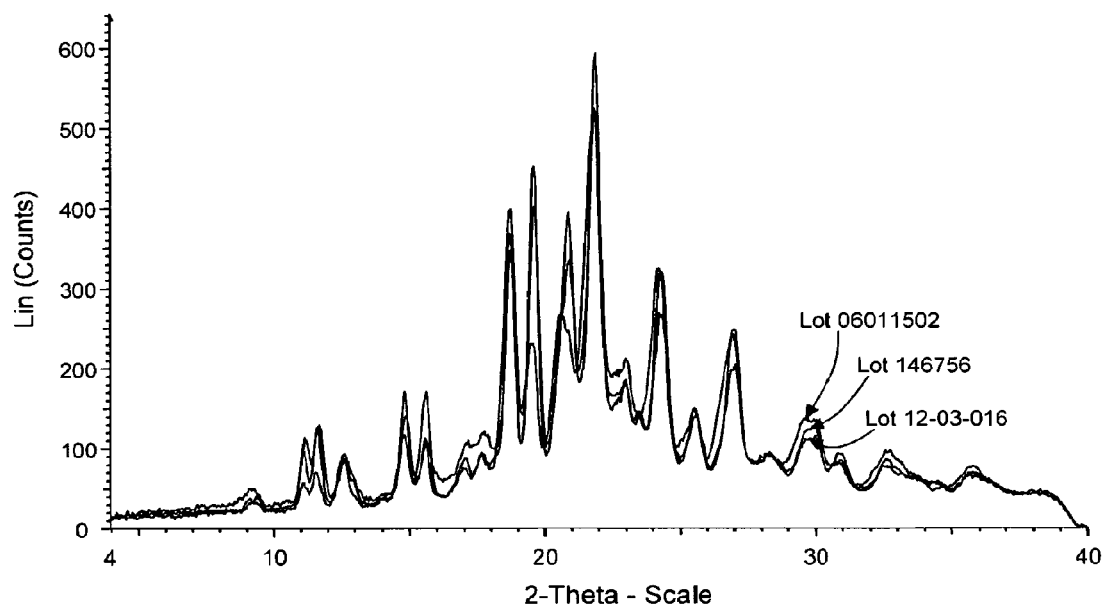
FIG. 5H shows the DSC plots of valomaciclovir samples lots 12-03-018, 06-01159-2 and 146756.
Figure 5I:
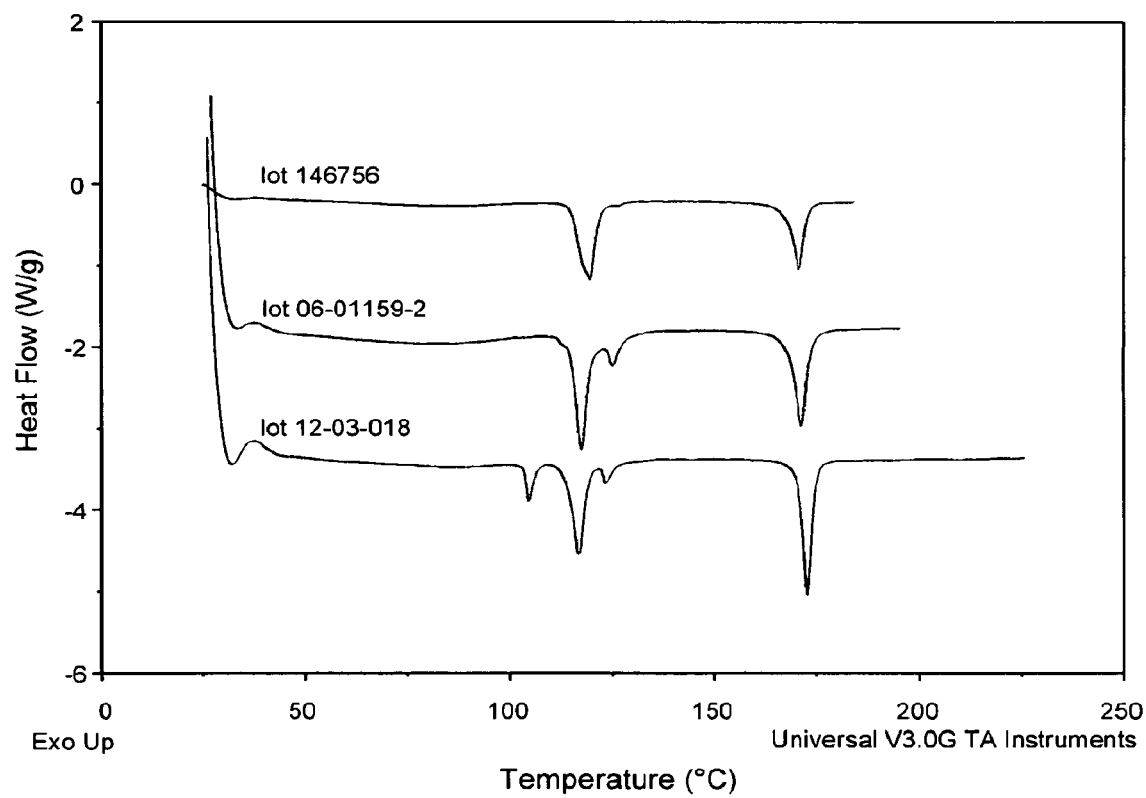
FIG. 5I shows the powder XRD patterns of valomaciclovir samples lots 12-03-018, 06-01159-2 and 146756.

The powder XRD patterns and DSC thermograms (FIGS. 5H and I) observed for Lot 12-03-018, Lot 146756 and Lot 06-01159-2 resemble those observed for Polymorph A. Nevertheless, the flowability and handleability of these materials was poor and/or inconsistent (Table 2). For example, the Lot 146756 material had a measured Carr Index of 64, indicating extremely poor flowability. The material also generated macroscopic agglomerations hundreds of microns in length. The macroscopic result was material that was tacky in nature with poor handleability and poor powder flow as determined by visual observation.

TABLE 2

Valomaciclovir batch physical characteristics:
Carr Index, particle size, and agglomerate size

| Batch | Polymorph Form | Carr Index | Typical Particle Size Range | Agglomerate Size |
|---|---|---|---|---|
| 146756 | A | 64 | 5-20 | 200 |
| 12-03-018 | A | 48 | 5-40 | 100 |
| 12-03-011 | B1 | 42 | 2-15 | 100 |

In some embodiments, a method for preparing Polymorph A as follows is provided. A mixture of valomaciclovir and a lower alkanol solvent in a ratio of 100 g valomaciclovir per liter of solvent was stirred and heated to an appropriate internal temperature to achieve complete dissolution. The solution was cooled with stirring under a controlled temperature gradient to effect substantial crystallization of valomaciclovir. The resulting mixture was filtered, the resulting solid air was dried and vacuum oven dried to afford a white solid, which is Polymorph A enriched valomaciclovir.

As used herein, the phrase "substantially the same X-ray diffraction pattern as shown in Table 1 or FIG. 2 means that in some embodiments, Polymorph A has 2-theta angles of 22.9°±0.2° and 18.6°±0.2°. It also means that in other embodiments, Polymorph A has 2-theta angles of 22.9°±0.2°, 18.6°±0.2°, 19.5°±0.2°, and 24.3°±0.2°. In still other embodiments, Polymorph A has 2-theta angles of 22.9°±0.2°, 18.6°±0.2°, 19.5°±0.2°, 24.3°±0.2°, 20.8°±0.2°, 21.8°±0.2°, and 27.0°±0.2°. In still other embodiments, Polymorph A has 2-theta angles of 22.9°±0.2°, 18.6°±0.2°, 19.5°±0.2°, 24.3°±0.2°, 20.8±0.2°, 21.8°±0.2°, 27.0°±0.2°, 14.7°±0.2°, and 15.5°±0.2°. In still other embodiments, Polymorph A has 2-theta angles of 22.9°±0.2°, 18.6°±0.2°, 19.5°±0.2°, 24.3°±0.2°, 20.8°±0.2°, 21.8±0.2°, 27.0±0.2°, 14.7°±0.2°, 15.5°±0.2°, 25.5°±0.2°, and 29.9°±0.2°.

As used herein, the phrase "substantially the same DSC thermograms as shown in FIG. 3" means that in some embodiments, Polymorph A has the characteristic DSC features of an endotherm from about 105° C. to about 125° C. and centered near 115° C. (typically 20-30 J/g) and a melting endotherm from about 170° C. to about 180° C., and centered near 171° C. (typically around 20-30 J/g).

The term "lower alkanol solvent" means any lower alkanol in which valomaciclovir is soluble and includes those primary, secondary and tertiary alcohols of from 1 to 6 carbon atoms. Suitable lower alkanol solvents include, for example, methanol, ethanol, 1-propanol, 2-propanol, 2-methyl-1-propanol, 2-methyl-2-propanol, 2,2-dimethyl-1-propanol and cyclohexanol. The lower alkanol solvent used in the preparation of the Polymorph A enriched valomaciclovir may be methanol, ethanol or 2-propanol. A 95:5 (v/v) ethanol/2-propanol may be used as a mixed solvent.

Typically, in accordance with some embodiments, the mixture of valomaciclovir and the solvent (pre-mixed if a mixed solvent is used) is heated with stirring to an appropriate internal temperature (for example, at from 65° C. to 74° C., or from 68° C. to 72° C., if ethanol or mixture of ethanol/2-propanol is used) to achieve almost complete dissolution. The heating process occurred over about one half hour. Stirring was continued optionally for another 30 minutes in order to achieve complete solution. The temperature was then set to cool at a rate of from 5° C. to 15° C. per hour, or from 8° C. to 12° C. per hour, with stirring throughout the cooling cycle. The solids by and large crystallized out of solution when the internal temperature reaches between 55° C. and 61° C. Stirring was continued for 1 to 4 hours after coming to room temperature (approximately 18 to 25° C.), the resulting mixture was filtered and the resulting wet cake was dried in a vacuum oven overnight (temperature 40 to 50° C., pressure 3-15 in. Hg, slow nitrogen sweep), to afford a white solid that was enriched in Polymorph A.

The combination of solvent selection and temperature controls make this process highly reproducible and scalable. This process has been tested on scales ranging from 10 g to 30 kg.

When other solvents or combinations are used, the temperatures, solubility, and loading profiles may be different than cited in the foregoing procedure, and can be adjusted accordingly by one of ordinary skill in the art in view of the instant disclosure.

In some embodiments, the mixed solvent used in the process of this invention is 95:5 (v/v) ethanol/isopropanol, which is equivalent to Specially Denatured Alcohol (SDA) 3C. Use of SDA 3C, a relatively low cost commercial product, makes this process more commercially viable.

Polymorph A is the most crystalline and thermodynamically the most stable polymorph of valomaciclovir. Competitive and non-competitive slurry experiments showed Polymorph A as the ending form regardless of the starting polymorph form. Solid powders of Polymorph A are more flowable, making it easier to be made into a tablet formulation.

In some embodiments, Polymorph A enriched valomaciclovir has substantially the same X-ray diffraction pattern as shown in Table 1 or FIG. 2.

In some embodiments, the Polymorph A enriched valomaciclovir has substantially the same DSC thermograms as shown in FIG. 3.

In some embodiments, the Polymorph A enriched valomaciclovir has an IR spectrum substantially conforming to a reference standard.

The flow characteristics of the solid products of this invention can be measured by the Carr index [Pharmaceutical Preformulation and Formulation, A practical guide from candidate selection to commercial dosage form, Mark Gibson, Ed.; Interpharm Press, 2002; pages 386-7.) By subjecting a powder to mechanical forces, resistance to powder flow can be observed. The increase in bulk density (compressibility) of a powder subjected to tapping can be used to determine the Carr index. In some embodiments, the Polymorph A enriched valomaciclovir has a Carr index value range from about 35 to about 50.

The particle size of the solid product of this invention can be evaluated in silicone oil using polarized light microscopy. In some embodiments, Polymorph A enriched valomaciclovir has particle size range from about 10 to about 300 microns as measured using this system.

In some embodiments, the Polymorph A enriched valomaciclovir is a white or light tan powder by visual inspection.

In some embodiments, Polymorph A enriched valomaciclovir forms a clear to practically clear solution when dissolved in a solvent, for example methylene chloride.

In some embodiments, Polymorph A enriched valomaciclovir has a residue on ignition of not more than 0.2%.

In some embodiments, heavy metals (as Pb) are present in the Polymorph A enriched valomaciclovir is no more than 0.002%.

In some embodiments, Polymorph A enriched valomaciclovir has a moisture content of not more than 1.0%. The moisture content can be analyzed by Karl Fischer titration.

The solvent content in the product of this invention can be determined by GC analysis. In some embodiments, Polymorph A enriched valomaciclovir conforms to the following standards with respect to residual solvents: NMT 0.5% for Acetone, Ethyl Acetate, Heptane, Isopropanol, Tetrahydrofuran, Ethyl Alcohol; NMT 0.1% for Acetonitrile, Dichloromethane, Toluene; NMT 0.05% for Ethylene Glycol Dimethylether; NMT 0.05% of any other individual solvent; NMT 1.0% total solvents.

The purity of a product and amount of impurities may be measured by HPLC analysis. In some embodiments, Polymorph A enriched valomaciclovir has a purity of not less than 970 µg/mg on the anhydrous and solvent free basis. In other embodiments, no single known impurity except for guanine stearate alcohol is present in greater than 1.5% in Polymorph A enriched valomaciclovir. In still other embodiments, guanine stearate alcohol is present in not greater than 2.5%. In still other embodiments, no single unknown impurity is present in greater than 1.0%. In still other embodiments, the total impurities present are no more than 3.0%.

In some embodiments, Polymorph A enriched valomaciclovir has a retention time not differing with a reference standard by more than 2.0%.

In some embodiments, Polymorph A enriched valomaciclovir conforms to the following standards with respect to diastereomeric and enantiomeric impurities: (S,S)-diastereomers not greater than 4.0%; (R,R)-diastereomer plus (S,R)-enantiomers not greater than 3.0%.

In some embodiments, Polymorph A enriched valomaciclovir has a potency of not less than 900 μg/mg on the anhydrous and solvent free basis. Potency is a quantitative measurement of purity of the composition.

In some embodiments, Polymorph A enriched valomaciclovir has two or more of the characteristics described above.

In some embodiments, Polymorph A enriched valomaciclovir has substantially the same X-ray diffraction pattern as shown in Table 1 or FIG. 2, substantially the same DSC thermograms as shown in FIG. 3, an IR spectrum substantially conforming to a reference standard, Carr index value range from about 35 to about 50, particle size range from about 10 to about 300 microns, a residue on ignition of not more than 0.2%, moisture content of not more than 1.0%, residual solvents not more than as defined above, and/or purity of not less than 97%.

In some embodiments, Polymorph A enriched valomaciclovir has substantially the same X-ray diffraction pattern as shown in Table 1 or FIG. 2, substantially the same DSC thermograms as shown in FIG. 3, an IR spectrum substantially conforming to a reference standard, Carr index value range from about 35 to about 50, particle size range from about 10 to about 300 microns, a residue on ignition of not more than 0.2%, moisture content of not more than 1.0%, residual solvents not more than as defined above, and purity of not less than 97%.

Other polymorphs of valomaciclovir include, but not limited to, Forms B1, B2, B3, B4, C, and H. These polymorphs are obtained using methods and conditions as described in Example 5—Polymorph Screening for Valomaciclovir herein. These polymorphic forms are useful as analytical standards in evaluating the polymorphic purity of valomaciclovir drug products. Polymorphs B1, B2, B3, B4, C and H are readily converted to Form A alone, or in combinations, using processes described herein, and therefore, can serve as source materials in producing Polymorph A enriched valomaciclovir composition of this invention.

In some embodiments, Polymorph A enriched valomaciclovir is substantially free of other polymorphic forms.

In some embodiments, Polymorph A enriched valomaciclovir is substantially free of Form B1.

In some embodiments, Polymorph A enriched valomaciclovir is substantially free of Form B2.

In some embodiments, Polymorph A enriched valomaciclovir is substantially free of Form B3.

In some embodiments, Polymorph A enriched valomaciclovir is substantially free of Form B4.

In some embodiments, Polymorph A enriched valomaciclovir is substantially free of Forms B1, B2, B3, or B4.

In some embodiments, Polymorph A enriched valomaciclovir is substantially free of Form C.

In some embodiments, Polymorph A enriched valomaciclovir is substantially free of Forms B1, B2, B3, B4, or C.

Also provided herein are methods for the treatment and/or prevention of viral infections comprising the administration of an therapeutically effective amount of the Polymorph A enriched valomaciclovir of the invention to a patient in need thereof.

The viral infections treatable using the methods described herein are caused by, for example, varicella zoster virus, herpes simplex viruses (HSV-1 and HSV-2), human herpes viruses (HHV-6, HHV-7 and HHV-8), Epstein Barr virus, cytomegalovirus, and HIV.

In some embodiments, the viral infection is a herpes virus infection selected from Varicella zoster, Herpes simplex viruses (HSV-1 and HSV-2), Human herpes virus 6, Human herpes virus 7, Human herpes virus 8, Epstein Barr virus, and cytomegalovirus. In these embodiments, the viral infection may be present as various forms of human disorder such as chicken pox, shingles, labial herpes/cold sores, genital herpes, mononucleosis, Kaposi's sarcoma, chronic fatigue, roseola infantum, multiple sclerosis, nasopharyngeal carcinoma and other malignant tumors.

In other embodiments, the viral infection is HIV or co-infected HIV/HBV or HIV/HCV or other opportunistic diseases, such as CMV or herpes keratis manifested by HIV infection or AIDS.

Polymorph A enriched valomaciclovir may be used in the manufacture of a medicament for the treatment or prophylaxis of viral infections, especially via oral or other systemic administration.

Polymorph A enriched valomaciclovir is crystalline, has good flow characteristics, and can be readily converted to tablets for oral administration using procedures and methods known in the art.

Additional embodiments of prophylaxis or treatment of viral infections comprise the use of the Polymorph A enriched valomaciclovir before, during or after transplantation.

In some embodiments, a polymorph described herein is co-administered typically orally or systemically, with an immunomodulator agent such as, for example, a glucocorticoid. Representative glucocorticoids include, but are not limited to, alclometasone, desonide, fluprednidene, flumethasone, hydrocortisone and its esters such as hydrocortisone butyrate or hydrocortisone acetate, clobetasone, triamcinolone acetonide, betmethasone, budenoside, desoximethasone, diflorosane, fluocinolone, fluoccinonide acetonide, fluocortolone, fluticasone, methylprednisolone aceponate, mometasone, rofleponide and the like. Glucocorticoids such as hydrocortisone or betamethasone or dextromethasone are typically administered in their conventional immunomodulatory dosage regimes.

For each of the above-indicated utilities and indications the amounts required of valomaciclovir API will depend upon a number of factors including the severity of the condition to be treated and the identity of the recipient and will ultimately be at the discretion of the attendant physician. In general however, a suitable effective dose will be in the range of 1 to 150 mg per kilogram bodyweight of recipient per day. Other suitable effective doses are in the range 5 to 120 mg per kilogram bodyweight per day (unless otherwise indicated, all weights of the active ingredients are calculated with respect to the valomaciclovir). The desired dose in a given day may be presented as one, two, three or four or more sub-doses administered at appropriate intervals throughout the day. These sub-doses may be administered in unit dosage forms, for example, containing about 50 to 2000 mg, or from about 250, 500, 1000, 2000 or 3000 mg of active ingredients per unit dose form. In some embodiments, a unit dose is 1000 mg/day.

The following dosage regimes are given for guidance: treatment of varicella zoster virus infections (for example shingles): a single daily dose of about 500 mg to 3 g is administered for three to seven days; alternatively, a total daily dose of about 500 mg to 3 g is administered at 250 mg to 1.5 g twice a day for three to seven days. For example, patients can be treated within 72 hours of the onset of the zoster rash with daily dose of 1000 mg, 2000 mg or 3000 mg for seven days. In some embodiments, a dosage regime for treatment or prevention of varicella zoster virus infections is 1 gm is administered for seven days. In other embodiments, a dosage regime for treatment or prevention of varicella zoster virus infections is 2 gm is administered for seven days.

The following dosage regimes are given for guidance: treatment of Epstein-Barr virus (for example, mononucleosis): a total daily dose of about 2.0 g is administered at 1.0 g twice a day for 7 to 21 days. For transplant patients, this daily dose is administered for three to six months for the period at risk; and for HIV positive patients the daily dose is administered as usually indicated for improving quality of life, for example for two years or more. In some embodiments, a dosage regime for treatment or prevention of Epstein-Barr virus (for example, mononucleosis) is 1 g is administered for seven days.

The following dosage regimes are given for guidance: suppression of human herpes virus 6A (HHV-6A): a total daily dose of 500 mg to 3.0 g is administered once daily for three to six months for the period at risk.

The following dosage regimes are given for guidance: suppression of human herpes virus 8 (HHV-8): a total daily dose of 500 mg to 3.0 g is administered once daily for three to six months for the period at risk.

The following dosage regimes are given for guidance: treatment of herpes simplex virus types 1 and 2 virus infection: a total daily dose of 1.0 to 4 g is administered (500 mg twice a day or 2.0 g twice a day for 5 to 10 days); suppression of herpes simplex virus types 1 and 2 infections: a total daily dose of a 250 mg to 1 g is administered for about one to ten years (depending on the subject).

While Polymorph A enriched valomaciclovir may be administered alone, for example, in a capsule, it may also be present as a pharmaceutical formulation. Such formulations comprise Polymorph A enriched valomaciclovir together with one or more acceptable carriers/excipients and optionally, other therapeutic ingredients. The carrier(s) must be acceptable in the sense of being compatible with the other ingredients of the formulation and not deleterious to the recipient.

The formulations include, but are not limited to, those suitable for rectal, nasal, topical (including buccal and sublingual), vaginal or parenteral (including subcutaneous, intramuscular, intravenous and intradermal) administration. In some embodiments, the formulation is an orally administered formulation. The formulations may conveniently be presented in unit dosage form, e.g., tablets and sustained release capsules, and may be prepared by any methods well known in the art of pharmacy.

Such methods include bringing the polymorph into association with the carrier. In general, the formulations are prepared by uniformly and intimately bringing Polymorph A enriched valomaciclovir into association with liquid carriers or finely divided solid carriers or both, and then shaping the product, if necessary. The invention extends to methods for preparing a pharmaceutical composition comprising bringing Polymorph A enriched valomaciclovir in conjunction or association with a pharmaceutically acceptable carrier or vehicle. If the manufacture of pharmaceutical formulations involves intimate mixing of pharmaceutical excipients, it is often the case that the excipients used are non-basic in nature, i.e., either acidic or neutral.

The formulations for oral administration of the present invention may be presented as discrete units such as capsules, cachets or tablets, each containing a predetermined amount of the active agent. Alternatively, they can be presented as a powder or granules such as a solution or a suspension of the active agent in an aqueous liquid, a non-aqueous liquid, an oil-in-water liquid emulsion, a water-in-oil liquid emulsion, a bolus, etc.

With regard to compositions for oral administration (e.g., tablets and capsules), the term "suitable carrier" includes vehicles such as common excipients, for example, binding agents such as syrup, acacia, gelatin, sorbitol, tragacanth, polyvinylpyrrolidone (Povidone), methylcellulose, ethylcellulose, sodium carboxymethylcellulose, hydroxypropylmethyl-cellulose, sucrose and starch; fillers and carriers, for example, corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavoring agents such as peppermint, oil of wintergreen, cherry flavoring or the like can also be used. It may be desirable to add a coloring agent to make the dosage form readily identifiable. Tablets may also be coated by methods well known in the art.

A tablet may be made by compression or molding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active agent.

Other formulations suitable for oral administration include lozenges comprising the active agent in a flavored base, usually sucrose and acacia or tragacanth; pastilles comprising the active agent in an inert base such as gelatin and glycerin, or sucrose and acacia; and mouthwashes comprising the active agent in a suitable liquid carrier.

In some embodiments, the pharmaceutical composition is a caplet which includes crystalline valomaciclovir, croscarmellose sodium, povidone K-30, Tween-80, Talc, and magnesium stearate. In other embodiments the pharmaceutical composition is a caplet which includes, crystalline valomaciclovir (77% w/w), croscarmellose sodium (13.90%, w/w), povidone K-30 (3.25%), Tween-80 (1.10%), Talc (4.10%), and magnesium stearate (0.74%).

In some embodiments, the above pharmaceutical composition was made by wet granulating crystalline valomaciclovir and croscarmellose sodium using povidone K-30 and Tween-80. The granules were then dried and then screened through a mesh screen (#16). The dried and screened granulation, croscarmellose sodium and talc powder were then blended. Magnesium stearate was added, the blended material was then screened through a #30 mesh screen, blended and then discharged. The material was then compressed using a high speed rotary tablet press and the caplets coated with Opadry II 33G99020 in Accela Cota. Carnuaba wax was then added to the coating pan and the caplets polished and then packaged.

In some embodiments, the tablet processing consists of wet granulation, drying, screening, blending and compression operations. Bulk caplets are coated with Opadry II blue 33G99020 and polished with Carnauba Wax NF.

The pharmaceutical compositions and/or polymorphs can be administered incombination with other antiviral agents, such as acyclovir, valciclovir, penciclovir, famciclovir, ganciclovir and its prodrugs, cidofovir, foscarnet and the like for herpes indications.

For HIV therapy the pharmaceutical compositions and/or polymorphs are typically co-administered with other HIV therapies to avoid the generation of drug escape mutants and to treat concomitant infections in immunocompromised individuals. However, certain anti-infectives can induce a synergistic response, allowing one or both of the active ingredients to be administered at a lower dose that the corresponding monotherapy. For example, in drugs prone to rapid metabolism by Cyp3A4, co-dosing with the HIV protease inhibitor ritonavir can allow lower dosage regimes to be administered. The polymorphs described herein and each further antiviral agent are typically co-administered at molar ratios reflecting their respective activities and bio-availabilities. Generally such ratio will be of the order of 250:1 to 1:250, or 25:1 to 1:25, relative to the polymorph, but may be lower, for instance in the case of cytochrome P450 antagonists such as ritonavir.

Representative HIV antivirals include, but are not limited to, nucleoside reverse transcriptase inhibitors (NRTI) such as alovudine (FLT), zidovudine (AZT, ZDV), stavudine (d4T, Zerit), zalcitabine (ddC), didanosine (ddI, Videx), abacavir, (ABC, Ziagen), lamivudine (3TC, Epivir), emtricitabine (FTC, Emtriva), racevir (racemic FTC), adefovir (ADV), entacavir (BMS 30 200475), alovudine (FLT), tenofovir disoproxil fumarate (TNF, Viread), amdoxavir (DAPD), D-d4FC (DPC-817), -dOTC (Shire SPD754), elvucitabine (Achillion ACH-126443), BCH 10681 (Shire), SPD-756, racivir, D-FDOC, GS7340, INK-20 (thioether phospholipid AZT, Kucera), 2'3'-dideoxy-3'-fluoroguanosine (FLG) and its prodrugs such as MIV-210 and reverset (RVT, D-D4FC, Pharmasset DPC-817).

Representative non-nucleoside reverse transcriptase inhibitors (NNRTI) include, but are not limited to, delavirdine (Rescriptor), efavirenz (DMP-266, Sustiva), nevirapine (BIRG-587, Viramune), (+)calanolide A and B (Advanced Life Sciences), capravirine (AG1549f S-1153; Pfizer), GW-695634 (GW-8248; GSK), MIV-150 (Medivir), MV026048 (R-1495; Medivir AB/Roche), NV-05 2 2 (Idenix Pharm.), R-278474 (Johnson & Johnson), RS-1588 (Idenix Pharm.), TMC-120/125 (Johnson & Johnson), TMC-125 (R-165335; Johnson & Johnson), UC-781 (Biosyn Inc.) and YM215389 (Yamanoushi).

Representative HIV protease inhibitors include, but are not limited to, PA-457 (Panacos), KPC-2 (Kucera Pharm.), HGTV-43 (Enzo Biochem), amprenavir (VX-478, Agenerase), atazanavir (Reyataz), indinavir sulfate (MK-639, Crixivan), Lexiva (fosamprenavir calcium, GW-433908 or 908, VX-175), ritonavir (Norvir), lopinavir+ritonavir (ABT-378, Kaletra), tipranavir, nelfinavir mesylate (Viracept), saquinavir (Invirase, Fortovase), AG1776 (JE-2147, KNI-764; Nippon Mining Holdings), AG-1859 (Pfizer), DPC-681/684 (BMS), GS224338 (Gilead Sciences), KNI-272 (Nippon Mining Holdings), Nar-DG-35 (Narhex), P(PL)-100 (P-1946; Procyon Biopharma), P-1946 (Procyon Biopharma), R-944 (Hoffmann-LaRoche), RO-0334649 (Hoffmann-LaRoche), TMC-114 (Johnson & Johnson), VX-385 (GW640385; GSK/Vertex), VX-478 (Vertex/GSK).

Other HIV antivirals include, but are not limited to, entry inhibitors, including fusion inhibitors, inhibitors of the CD4 receptor, inhibitors of the CCRS coreceptor and inhibitors of the CXCR4 coreceptor, or a pharmaceutically acceptable salt or prodrug thereof. Examples of entry inhibitors are AMD-070 (AMD11070; AnorMed), BlockAide/CR (ADVENTRX Pharm.), BMS 806 (BMS-378806; BMS), Enfurvirtide (T-20, R698, Fuzeon), KRH1636 (Kureha Pharmaceuticals), ONO-4128 (GW-873140, AK-602, E-913; ONO Pharmaceuticals), PRO-140 (Progenics Pharm), PRO-542 (Progenics Pharm.), SCH-D (SCH417690; Schering-Plough), T-1249 (R724; RocheTrimeris), TAK-220 (Takeda Chem. Ind.), TNX-355 (Tanox) and UK 427,857 (Pfizer). Examples of integrase inhibitors are L-870810 (Merck & Co.), c-2507 (Merck & Co.) and S(RSC)-1838 (shionogi/GSK).

The invention will now be illustrated by Examples. The Examples are not intended to be limiting of the scope of the present invention but instead should be read in conjunction with the detailed and general description above, to provide further understanding of the invention and outline a process for preparing the intended product of the process of the invention as well as other aspects of the invention.

EXAMPLES

Example 1

Certificate of Analysis for Valomaciclovir API

The Certificate of Analysis for valomaciclovir API Lot A501S8-07-001 is shown in Table 3 to demonstrate the analytical data obtained for the product of this invention.

TABLE 3

Certificate of Analysis for Valomaciclovir API

| Test | Specification |
| --- | --- |
| Description | White to light tan powder |
| Identification (IR) | Conforms to reference |
| Moisture (KF) | NMT 1.0% |
| Solution Clarity | Clear to practically clear; a few fibers may be present |
| Residue on Ignition | NMT 0.2% |
| Heavy Metals (as Pb) | NMT 0.002% |
| Diastereomeric and Enantiomeric Impurities | (S,S)-Diastereomer not greater than 4.0%; (R,R)-Diastereomer plus (S,R) Enantiomer not greater than 3.0% |
| Potency (HPLC) | Not less than 900 mcg/mg on the anhydrous and solvent free basis |
| Purity (HPLC) | Not less than 970 mcg/mg on the anhydrous and solvent free basis |
| Identification | Retention time of the sample and of the reference standard do not differ by more than 2.0% |

TABLE 3-continued

Certificate of Analysis for Valomaciclovir API

| Test | Specification |
|---|---|
| Residual solvents | NMT 0.5% for Acetone, Ethyl Acetate, Heptane, Isopropanol, Tetrahydrofuran, Ethyl Alcohol; NMT 0.1% for Acetonitrile, Dichloromethane, Toluene; NMT 0.05% for Ethylene Glycol, Dimethylether; NMT 0.05% of any other individual solvent; NMT 1.0% total solvents |
| Impurities (HPLC) | No single impurity greater than 1.5%; Guanine Stearate Alcohol: NMT 2.5% Known impurities: C16 ester; N-7 isomer; N-ethyl valine; Regioisomer; Guanine Stearate Alcohol (IV); C20 ester; Stearate Aldehyde (III); Guanine Stearate (II); O,O Distearate; V Boc; No single unknown impurity >1.0%; Total impurities NMT 3.0% |

Example 2

Recrystallization Process for Valomaciclovir Polymorph A

To a 2 L round bottom flask, equipped with mechanical stirring, oil bath controlled by a model 210 T J KEM temperature controller/thermocouple, internal thermocouple attached to a Yokagowa temperature recorder and a drying tube was added 110 g of EPB 348 lot 146756, 1.1 L of a premixed solution consisting of 55 mL of 2 propanol (Fisher, lot 050564) and 1045 mL of 200 proof ethanol (Aaper, lot 06128WA) (The equivalent of SDA 3C Denatured anhydrous alcohol). The resulting stirred mixture was heated to an internal temperature of 72° C., which achieved almost complete dissolution of the solids. The heating process occurred over about one half hour. The bulk of the solids went into solution readily; the last bits required stirring at about 72° C. internal temperature for 30 minutes to achieve complete dissolution. The internal temperature was allowed to reach as high as 74° C.* The solution was then cooled at a rate of 10° C. per hour**, with stirring throughout the cooling cycle. The solids by and large crystallized out of solution when the internal temperature reached between 55 and 61° C. There was a 2° C. exotherm as a result of the crystallization. Stirring was continued for one hour after coming to room temperature (approximately 25° C.), the resulting mixture was filtered and the resulting solid was air dried and then vacuum oven dried overnight (50° C., approximately half an atmosphere of vacuum, slow nitrogen sweep), to afford 106 g of a white solid (52772-10-6).

\* HPLC evidence (Column: Phenomenex INERSIL ODS-2, 250×4.6 mm, 5 micron particle size; Mobile Phase: 0.2% perchloric acid in 62:38 Acetonitrile:water/Acetonitrile; Gradient: 0 to 95% over 25 minutes; Flow Rate: 1.5 mL/min; Detection: 254 nm) suggests that by extending the timing of the crystallization (to include an overnight stir of the suspension after crystallization), an impurity (guanine stearate alcohol) builds to about 0.9 area %, from an original starting level of about 0.3 area %. By following the times and temperatures quoted, the build of the impurity is limited to 0.6 area %, which is currently considered acceptable.

\*\* Cooling rates ranging from 5 C per hour about 12 C per hour have been explored, and found to afford product of comparable chemical purity and polymorphic form.

The characteristics of the product have diffraction characteristics similar to those found in FIGS. 2 and 3, which are representative of valomaciclovir Polymorph A.

Example 3

Crystallization Process Development

Small scale (1-5 g) crystallizations were performed using lot 146756 as stock material. Several solvents were identified that tended to produce nice solids of the material (pyridine, DMF, ethanol, etc). Because of the low viability of many of these solvents and the promise exhibited by ethanol, ethanol was chosen for further study.

First 10-g Scale Recrystallization

A 10.1 g sample of EPB 348 (lot #146756) was recrystallized from 100 mL of absolute ethanol (Aaper USP). The internal temperature needed to be raised to 68° C. before complete dissolution was achieved. The solution was stirred at 75° C. for one hour, then heating was stopped, and the stirred mixture was allowed to slowly cool to room temperature overnight, while magnetically stirred. The resulting crystal mass was filtered, dried to constant weight at 50 C to afford 9.3 g of a white solid (sample 52772-2-7).

Second 10-g Scale Recrystallization

In order to demonstrate reproducibility, the process was repeated, starting with 10.0 g of the same lot of EPB 348. After isolation and drying, this afforded 9.3 g of a white solid (sample 52772-3-17). By proton NMR, this material was consistent with the original sample of EPB 348.

Third 10-g Scale Recrystallization

Figure 6:
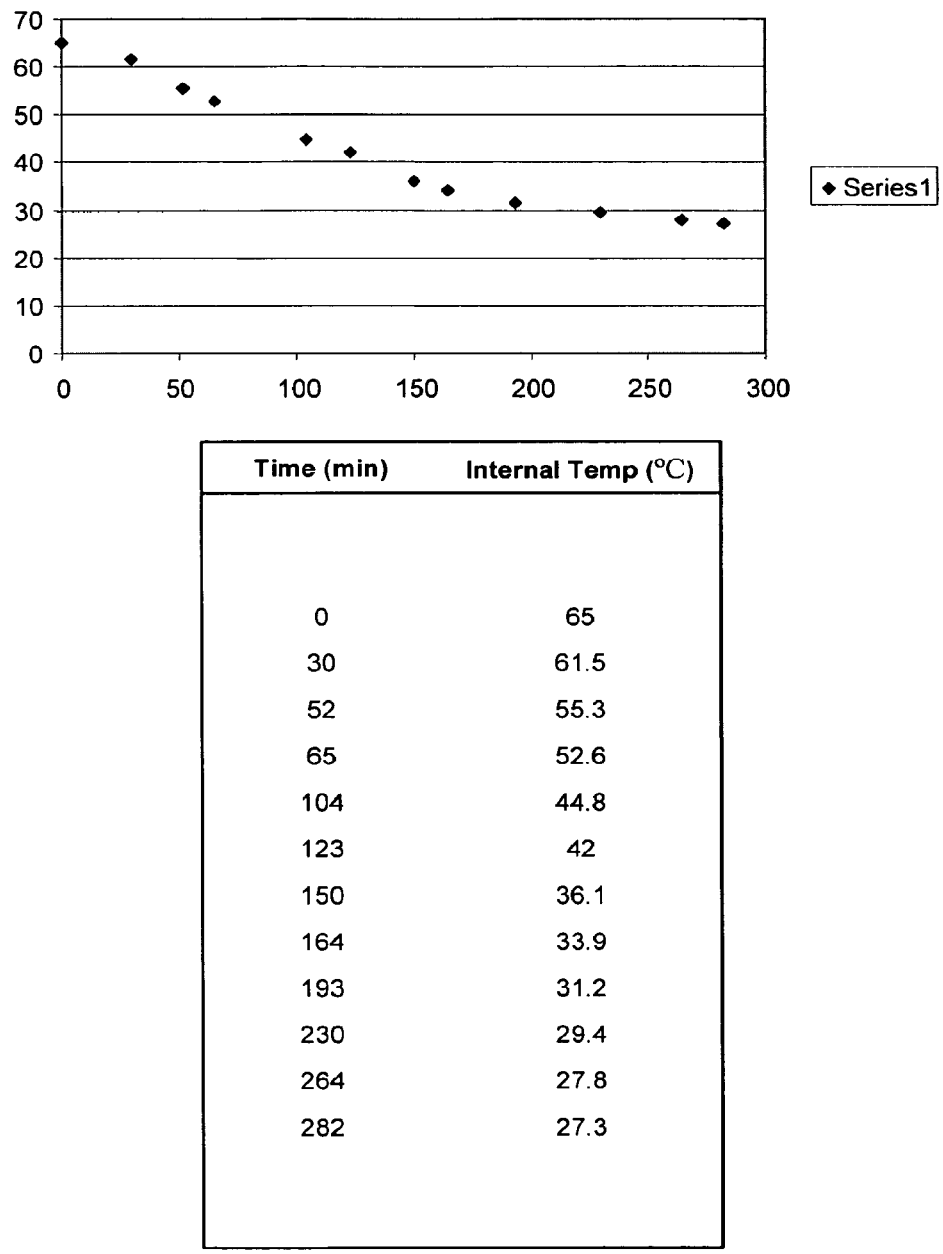
FIG. 6 shows a cooling curve in the recrystallization process.

In order to make the process more commercially viable, the process was repeated, but using freshly prepared denatured alcohol, which was equivalent to Specially Denatured Alcohol (SDA) 3C. This was prepared by adding 5 volumes of 2-propanol to 95 volumes of absolute ethanol, and the resulting solution mixed thoroughly. To 100 mL of this 3C denatured alcohol was added 10.0 g of EPB 348, and the resulting mixture heated to an internal temperature of 70° C. and was allowed to slowly come to room temperature, while being stirred magnetically. The internal temperature was periodically noted, and is graphed as shown in FIG. 6. The mixture was a complete solution at 61.5° C., but had formed solids by the time it had cooled to an internal temperature of 55.3° C. After the stirred suspension had cooled to room temperature it was filtered, air dried, then vacuum oven dried (50° C., approximately half an atmosphere vacuum, with slow nitrogen sweep), to afford 9.37 g of a while solid, sample 52772-5-8.

First 100-g Scale Recrystallization

The recrystallization from SDA 3C alcohol was repeated, on larger scale, controlling the cool down curve at 5° C. per hour, and capturing a record of the internal temperature throughout the cool down. To a 2 L round bottom flask, equipped with mechanical stirring, oil bath controlled by a model 210 T J KEM temperature controller/thermocouple, internal thermocouple attached to a Yokagowa temperature recorder, drying tube was added: 110 g of EPB-348 lot 146756, 1.1 L of a premixed solution consisting of 55 mL of 2-propanol (Fisher, lot 050564) and 1045 mL of 200 proof ethanol (Aaper, lot 06128WA). The resulting stirred mixture was heated to an internal temperature of 72° C., which achieved complete dissolution. The temperature was then set to cool at a rate of 5° C. per hour, with stirring throughout the cooling cycle. The solids crystallized out of solution when the internal temperature reached between 60 and 61° C. Stirring was continued overnight, and then the resulting mixture was filtered, and the resulting solid was air dried and then vacuum oven dried (50° C., approximately half an atmosphere of vacuum, slow nitrogen sweep), to afford 106.7 g of a white solid (52772-8-10).

Additional 100-g Scale Recrystallization

Two additional batches of EPB-348 were recrystallized from lot 146756 at the 100 g scale in 3C ethanol as described previously. The changes to the process included 1) faster isolation (solids were filtered after the solutions reached ambient temperature rather than standing in the mother liquor overnight) and 2) cooling rates of 10 and 15° C./hr were targeted rather than the 5° C./hr used on the previous 100 g batch.

The first batch was cooled at ~10° C./hr and the second batch was cooled at an initial rate of 13° C./hr which slowed to about 12° C. per hour due to warm ambient temperature conditions. The batches were designated 52772-10-6 and 52772-12-27 respectively. Both batches were isolated after cooling to ambient temperature to yield nice solids and were analyzed by XRD for polymorphic form and HPLC for impurity profile.

Diffraction and Thermal Characteristics

Figure 7:
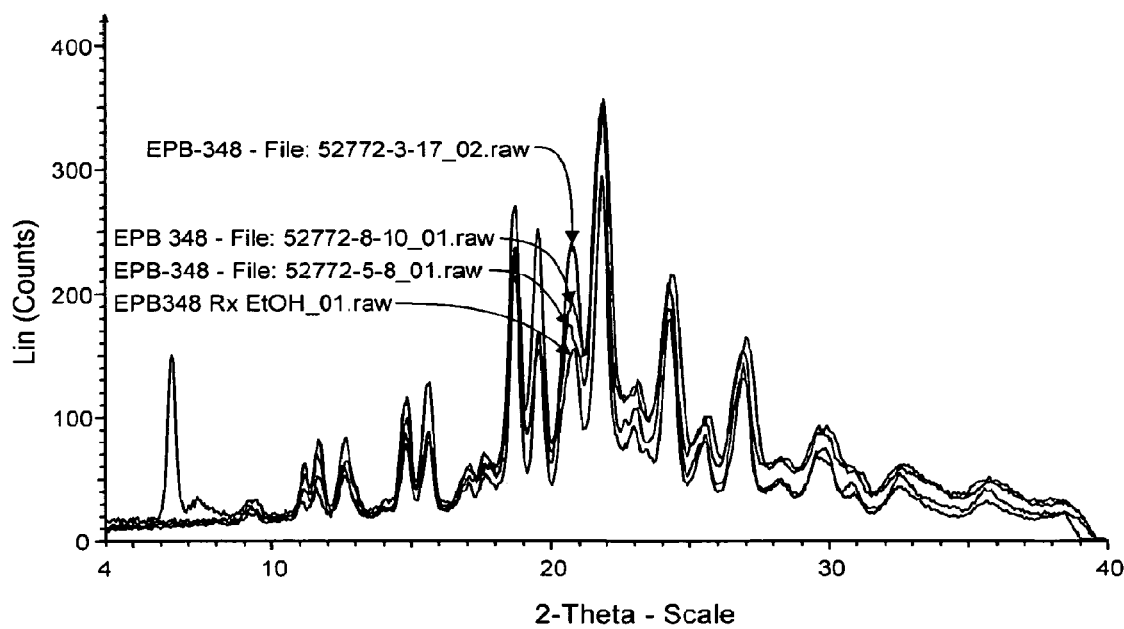
FIG. 7 shows the X-ray diffraction patterns of recrystallized valomaciclovir samples.
Figure 8:
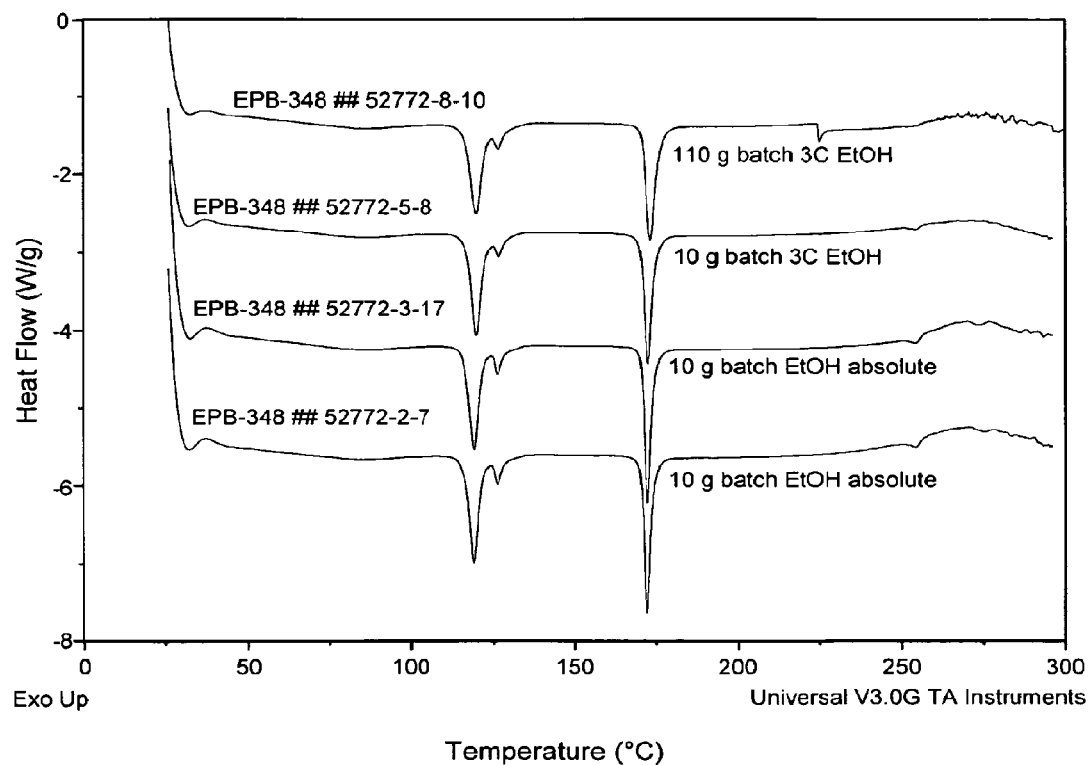
FIG. 8 shows the DSC thermograms of recrystallized valomaciclovir samples.

The X-ray diffraction patterns and DSC thermograms of the samples from above recrystallization processes on 10-gram scales are shown in FIGS. 7 and 8 respectively. Both the X-ray diffraction and the thermal characteristics of the crystallized samples are consistent with Polymorph A.

Particle Size and Flow Characteristics

By subjecting a powder to mechanical forces, resistance to powder flow can be observed. The increase in bulk density (compressibility) of a powder subjected to tapping can be used to determine the Carr index. This index was measured for each of the four recrystallized batches and tabulated below.

Polarized light microscopy was used to evaluate the particle size range of the recrystallized samples in silicone oil. The particle size range is reported in Table 4 along with the powder flow data.

Overall, the Carr Index ranged from 38 to 56. Carr Indices improved with increasing particle size, which appeared to be related to the increase in scale. Material prepared by this method had better handling and powder flow than previous batches as determined by visual observation.

TABLE 4

Carr Index and Particle Sizes of Recrystallized Valomaciclovir Samples

| Batch | Description | Carr Index | Typical Particle Size Range |
|---|---|---|---|
| 52772-2-7 | $1^{st}$ 10 g | 53 | 20-50 |
| 52772-3-17 | $2^{nd}$ 10 g | 56 | 10-30 |

TABLE 4-continued

Carr Index and Particle Sizes of Recrystallized Valomaciclovir Samples

| Batch | Description | Carr Index | Typical Particle Size Range |
|---|---|---|---|
| 52772-5-8 | $3^{rd}$ 10 g | 44 | 35-50 |
| 52772-8-10 | 110 g | 38 | 150-300 |

HPLC analysis was performed on the four batches of recrystallized material. (Column: Phenomenex INERSIL ODS-2, 250×4.6 mm, 5 microm particle size; Mobile Phase: 0.2% perchloric acid in 62:38 Acetonitrile:water/Acetonitrile; Gradient: 0 to 95% over 25 minutes; Flow Rate: 1.5 mL/min; Detection: 254 nm) Samples were compared to lot 146756 which was used as the starting material for the recrystallization.

TABLE 5

Purity of Valomaciclovir Samples by HPLC

| Analytical Sequence | Batch | Description | HPLC (area %) |
|---|---|---|---|
| 1 | Lot 146756 | Starting material | 98.8 |
|  | 52772-2-7 | First 10 g | 98.8 |
|  | 52772-3-17 | Second 10 g | 98.8 |
|  | 52772-5-8 | Third 10 g | 98.9 |
|  | 52772-8-10 | First 100 g | 98.4 |
| 2 | Lot 146756 | Starting material | 99.1 |
|  | 52772-10-6 | Second 100 g | 98.8 |
|  | 52772-12-27 | Third 100 g | 98.7 |

Figure 9:
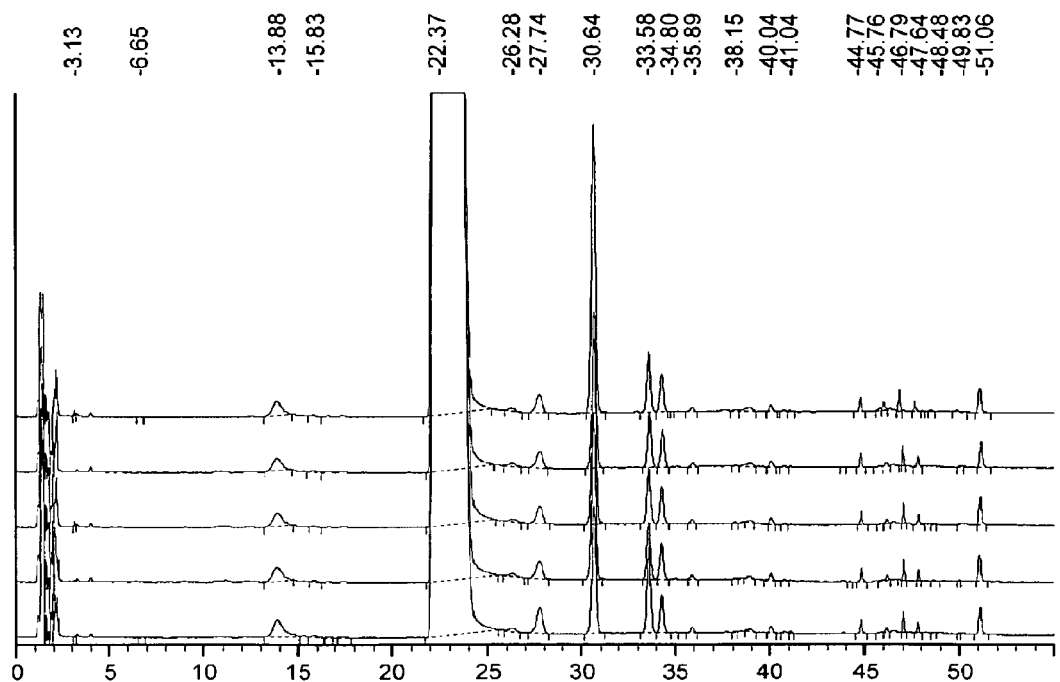
FIG. 9 shows HPLC overlay plot of 10-100 g batches of Polymorph A.

In general, the impurity profiles of the ethanol recrystallized material were similar to the starting material. Individual impurities below 0.05 area percent were not integrated. The samples from the three 10 g scale crystallization and the first 100 g scale crystallization were analyzed together (Analytical Sequence 1). The main impurities are listed in Table 6 by retention time. An HPLC overlay plot is shown in FIG. 9 showing representative chromatograms.

TABLE 6

Impurity Profile of Recrystallized Valomaciclovir (Batches 52772-2-7, 52772-3-17, 52772-5-8 and 52772-8-10)

| Impurity | Approximate Area % | Change during recrystallization |
|---|---|---|
| RRT 0.62 | 0.1 | Slight reduction |
| RRT 1.24 | 0.1 | Slight reduction |
| RRT 1.37 | 0.3 to 0.9 | Increases |
| RRT 1.50 | 0.2 | Slight reduction |
| RRT 1.53 | 0.1 | Doesn't change |
| RRT 2.27 | 0.05 | Doesn't change |

There were six impurities >0.05 area %. The impurities at RRT 0.62, 1.24, and 1.50 were reduced for all the recrystallized samples.

Two of the impurities, RRT 1.53 and RRT 2.27, did not appear to change during recrystallization.

One of the impurities, RRT 1.37, was observed to be elevated in the recrystallized material.

No new impurities were observed in the recrystallized materials.

The impurity at RRT 1.37 grows in each sample over time. It was observed to increase from 0.3 to 0.5 over about 14 hours at ambient temperature in the "standard" solution. While this impurity is observed to grow slowly over time, the lack of solution stability during the analysis does not explain the changes observed for this impurity.

The samples from the two additional 100 g scale crystallization were analyzed together (Analytical Sequence 2). The main impurities are listed in Table 7 by retention time.

TABLE 7

Impurity Profile of Recrystallized Valomaciclovir
(Batches 52772-10-6 and 52772-12-27)

| Impurity | Approximate Area % | Change during recrystallization |
|---|---|---|
| RRT 0.64 | 0.1 | Doesn't change |
| RRT 1.31 | 0.1 | Slight reduction |
| RRT 1.54 | 0.26 to 0.62 | Increases |
| RET 1.72 | 0.2 | Slight reduction |
| RRT 1.76 | 0.1 | Doesn't change |
| RRT 2.73 | 0.05 | Doesn't change |

The first observation comparing data from the two HPLC runs is that the retention times of the signals were different. This was attributed to running on a different HPLC with a cooled autosampler tray (Sequence 2), premixed mobile phase preparation, and other subtle differences. The retention times were within the system suitability criteria of the method.

The second point is that the same general trend in impurity separation during crystallization was observed. The main issue was the impurity at RRT 1.54 (corresponds to the impurity at RRT 1.37 previously). The impurity is still observed to increase upon recrystallization; however, the amount of growth of this impurity appears to have been lessened due to the faster isolation (not letting the solids ripen overnight before harvesting) and faster cooling rates (less time exposure to elevated temperatures).

The HPLC data indicate that the starting batch (146756) had about 0.26 area % of RRT 1.54 which grew to 0.55 and 0.62 area % in the second and third recrystallized 100 g batches. A chilled autosampler tray was used to minimize any growth in this impurity during the HPLC analysis.

No new impurities were observed in the two new recrystallized batches (above 0.05 area %).

The HPLC results indicate by using a cooling rate of 10 to 12-13° C./hr and collecting the solids after room temperature was reached, build up of the impurity at RRT 1.54 (RRT 1.37 previously) was slightly reduced.

Note that retention times may vary depending on the HPLC instrument used. Internal standards were used as controls.

LCMS Analysis

LCMS analysis was used to confirm the identity of the impurity that was growing (or concentrating) in the isolated product. The HPLC conditions from the supplied method were used to produce the same impurity profile on an LCMS as observed using HPLC. An LCMS amenable acid (TFA) was substituted for perchloric acid as called for in the LC method.

The suspicion was that this major impurity was the des valine analogue of valomaciclovir. The structure of the putative impurity is shown below.

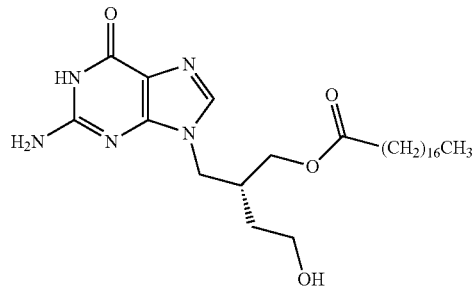

$C_{28}H_{49}N_5O_4$
m/e: 519.38 (100%), 520.38 (33.9%), 521.39 (5.0%), 521.38 (1.0%)
C, 64.71, H, 9.50, N, 13.48, O, 12.31

The parent API was observed to have an m/z of 619.4 in the positive ion mode which is consistent with the doubly esterified prodrug. The main impurity (via diode array) was observed to have an m/z of 520.3 consistent with $MH^+$ of the parent structure after removal of the valine substituent (as shown above).

It was tentatively concluded that the impurity growing during recrystallization was the des valine impurity.

Residual Solvent Analysis

GC analysis for isopropanol (IPA) and ethanol were performed on the batches of valomaciclovir recrystallized at the 10 and 100 g scales using the crystallization process reported earlier. The results of each batch are summarized in Table 8. The samples were analyzed using a 3 point calibration curve at 0.5, 1, and 1.5 times the ICH limits (5000 ppm) for ethanol and IPA. Spike recoveries to the sample solutions were also made to demonstrate suitable recoveries in the sample matrix.

TABLE 8

Residual Solvent Analysis 10-100 g Scale Polymorph A Batches

| Batch | Description | Ethanol (ppm) | IPA (ppm) |
|---|---|---|---|
| 52227-2-7 | First 10 g | <1990 | ND |
| 52772-3-17 | Second 10 g | <1905 | ND |
| 52772-5-8 | Third 10 g | ND | <1870 |
| 52772-8-10 | First 100 g | <1945 | <1865 |
| 52772-12-27 | Third 100 g | <1950 | <1865 |
| Spike Recovery | NA | 97.1% | 95.8% |

The results of the GC residual solvent analysis indicate that significant amounts of EtOH and IPA are not being retained by the product. The spike recoveries indicate that the analytes respond suitably for analysis.

Example 4

Large Scale Recrystallization Process for Valomaciclovir Polymorph a

Two additional batches of valomaciclovir were recrystallized from lot 146756 at the 4+ kg scale in 3C ethanol as described previously. Both batches resulted in nice, white material that was confirmed by XRD to be Polymorph A.

Each of the 4+ kg batches was characterized under Good Laboratory Practices (GLP). The results indicate the crystallization process produces acceptable results at the multi-kilogram scale.

30 Kg Scale Recrystallization

To a mixture of 184.7 kg of ethyl alcohol 200 Proof and 12.6 kg of isopropyl alcohol was added 31.6 kg of valomaciclovir, and the resulting mixture heated to an internal temperature of 68.2° C. (started from 18.4° C.) over 20 min, resulting in a clear solution. The solution was cooled at a cooling rate of 10-15° C. per hour to room temperature (20.0° C.) over 4 hours, while being agitated. The mixture was agitated for another 4 hours at 20° C. and was let stand for additional 7 hours before filtration. The solid residue was washed with a mixture of 69.8 kg of ethyl alcohol and 3.6 kg of isopropyl alcohol, resulting in a 69.3 kg wet cake. The wet cake was dried in a vacuum oven (<45° C., ~27 in. Hg vacuum, with slow nitrogen sweep), to afford 29.8 kg of a while solid, Batch A501 S8 07 001.

Example 5

Polymorph Screening for Valomaciclovir

A polymorph screening study was performed on valomaciclovir active pharmaceutical ingredient. The screen entailed recrystallizing the material using solvent recrystallization, recrystallization from the melt, annealing experiments, and slurry experiments. Overall, the API was recrystallized under more than 100 different crystal growth conditions and analyzed using powder x-ray diffraction. A chemometric treatment of the x-ray data was used to categorize the samples into different groups. These groups were studied using thermal, optical, spectroscopic and other tools to elucidate which groups represent unique solid state forms of the API.

In general, the API exhibits many different polymorphic forms, many of which appear to have low order. None of the solid state forms identified were solvates or hydrates. In addition to the polymorphic forms, the material also appears to exist in a liquid crystal state. The most stable polymorphic form identified during the study was designated as Form A (Polymorph A).

Solvent Recrystallization

To perform the solvent-based portion of the polymorph screen, the test material was solvent recrystallized under approximately 100 different crystal growth conditions. The scale of the recrystallization experiments was approximately 15 raL. The primary means of changing the crystal growth conditions was accomplished by using binary gradient arrays of solvent mixtures. The saturation temperature, growth temperature, and evaporation rate (relative supersaturation) were also varied to create additional differences in crystal growth conditions.

Overall, the polymorph screen was divided into four different recrystallization panels. Solids generated from the four recrystallization panels were analyzed by powder XRD along with samples generated by other means (slurry, annealing, etc). To mitigate the grain effects, a two dimensional detection system was used to collect all the XRD screening data. The XRD data collected was evaluated using a full profile chemometric treatment to determine if the crystalline form of the samples had changed upon recrystallization. Recrystallization panels are shown in FIG. 10A, FIG. 10B, FIG. 10C, and FIG. 10D. FIG. 10A shows Polymorph Screening Recrystallization Panel 1; FIG. 10B shows Polymorph Screening Recrystallization Panel 2; FIG. 10C shows Polymorph Screening Recrystallization Panel 3; and FIG. 10D shows Polymorph Screening Recrystallization Panel 4.

The chemometric analysis of the diffraction data categorized the samples into 8 different groups (or clusters) labeled A through H. There were three main groups and five groups with a small number of members. The recrystallized samples ranged from fully crystalline to fully amorphous (or liquid crystal) indicating a suitable range of crystallization rates were explored during the study.

Group A contained 24 members. Some of the "as received" batches fell into this group. This group had high crystallinity relative to the other groups.

Group B was the largest group and contained 43 members. This group had low crystallinity and was eventually subdivided into additional groups (B1 through B4).

Group C contained 23 members. This group represented amorphous or LC samples.

The other 5 groups (D through H) each had a small number of members (1 or 2 members). A summary showing the number of members in each group (A through H) is shown in Table 9. The resulting group designation for each individual (solvent based) recrystallization experiment is shown in the lower portions of FIGS. 10-A through D.

TABLE 9

Approximate Number of Members in Each Group

| Group | Members |
|---|---|
| A | 24 |
| B1 | 43 |
| B2 | |
| B3 | |
| B4 | |
| C | 23 |
| D | 2 |
| E | 1 |
| F | 2 |
| G | 1 |
| H | 1 |

Non-Competitive Slurry Experiments

In addition to the solvent recrystallization experiments, noncompetitive slurry experiments were also performed to search for new solid state forms. These experiments rely on solubility differences of different polymorphic forms (if the compound exists in different polymorphic forms). As such, only polymorphic forms (and solvates) having a lower solubility (more stable) than the crystalline form initially dissolved can result from a noncompetitive slurry experiment.

Essentially, when a solid is dissolved in a (slurry) solvent, a saturated solution eventually results. The solution is saturated with respect to the polymorphic form dissolved. However, the solution is supersaturated with respect to any polymorphic form which is more stable (more stable forms have lower solubilities) than the polymorphic form initially dissolved. Therefore, any of the more stable polymorphic forms can nucleate and precipitate from solution. In addition, noncompetitive slurry experiments are often useful in identifying solvents that form solvates with the API.

The slurry experiments were performed by exposing excess material to a small volume of neat solvents and agitating the resulting suspensions for approximately 1 week at ambient temperature. The solids were mechanically filtered and analyzed by XRD to determine the resulting form. To avoid possible desolvation or physical change after isolation, the samples were not subjected to drying before x-ray analysis. Table 10 shows the results of these noncompetitive slurry experiments.

TABLE 10

Non-Competitive Slurry Experiments Starting With Form A

| Solvent | Group of Initial Form | Temp (° C.) | Duration | Group of Final Form |
| --- | --- | --- | --- | --- |
| 1-propanol | A | 25 | 1+ week | A |
| Acetonitrile | A | 25 | 1+ week | A |
| EtOH | A | 25 | 1+ week | A |
| EtOAc | A | 25 | 1+ week | A |
| Heptane | A | 25 | 1+ week | A |
| IPA | A | 25 | 1+ week | A |
| Isopropyl acetate | A | 25 | 1+ week | A |
| Isopropyl Ether | A | 25 | 1+ week | A |
| MeOH | A | 25 | 1+ week | D |
| MTBE | A | 25 | 1+ week | A |
| Nitromethane | A | 25 | 1+ week | A |
| Pet Ether | A | 25 | 1+ week | A |
| sec-Butanol | A | 25 | 1+ week | A |
| Toluene | A | 25 | 1+ week | A |
| Water | A | 25 | 1+ week | A |

Most of the slurry experiments resulted in no significant change to the starting polymorphic form based on x-ray scattering behavior. One solvent, MeOH, did change the diffraction characteristics of the solids sufficiently to change the group that it belonged to. The additional studies performed on this sample are detailed further in the section labeled "Characterization of Groups".

Annealing Experiments

In addition to the solvent recrystallization experiments and noncompetitive slurry experiments, annealing experiments were performed to search for new solid state forms. These experiments entailed looking for structural changes as a function of temperature. This was accomplished using variable temperature powder x-ray diffraction, hot-stage microscopy, and DSC experiments to search for phase transitions that may exist in a polymorphic system.

The bulk of this work was aimed at understanding the thermal features of the various forms. By heat annealing samples and looking for changes in thermal, x-ray, optical, etc. behavior, a determination could be made as to whether new solid state forms resulted.

Recrystallization from the Melt

Recrystallization from the melt was performed by using HS microscopy or a DSC to heat the samples through melting and then attempt to crystallize them by cooling to different temperatures, or cooling them at different rates. Samples were then analyzed by XRD, DSC, etc. to determine if a different crystalline form was observed.

Characterization of Groups

After codifying the recrystallization data into different groups based on diffraction behavior (see Table 7), each group was studied to determine if other properties of the groups could be differentiated. The characterization of each group began by comparing the diffraction data representative of each group with the other groups. This was generally followed by DSC analysis, TGA analysis, hot stage microscopy, NMR analysis and other analyses.

Group A

Figure 11A:
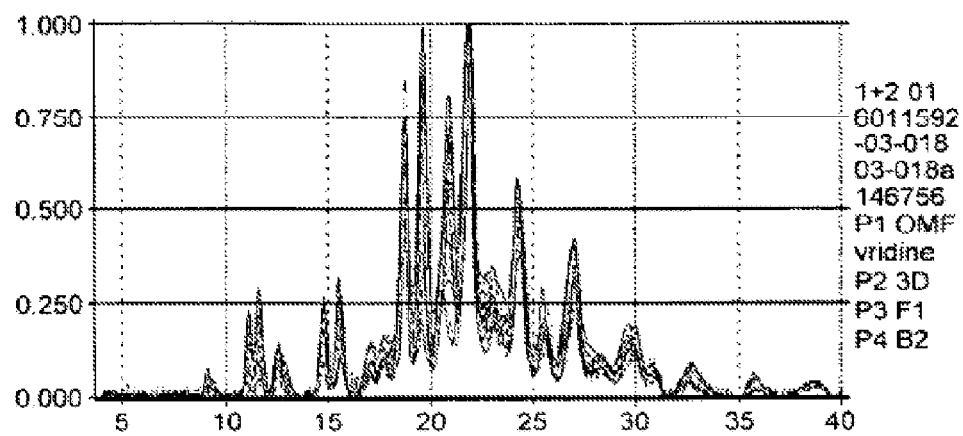
FIG. 11A shows diffraction characteristics of Group A.
Figure 11B:
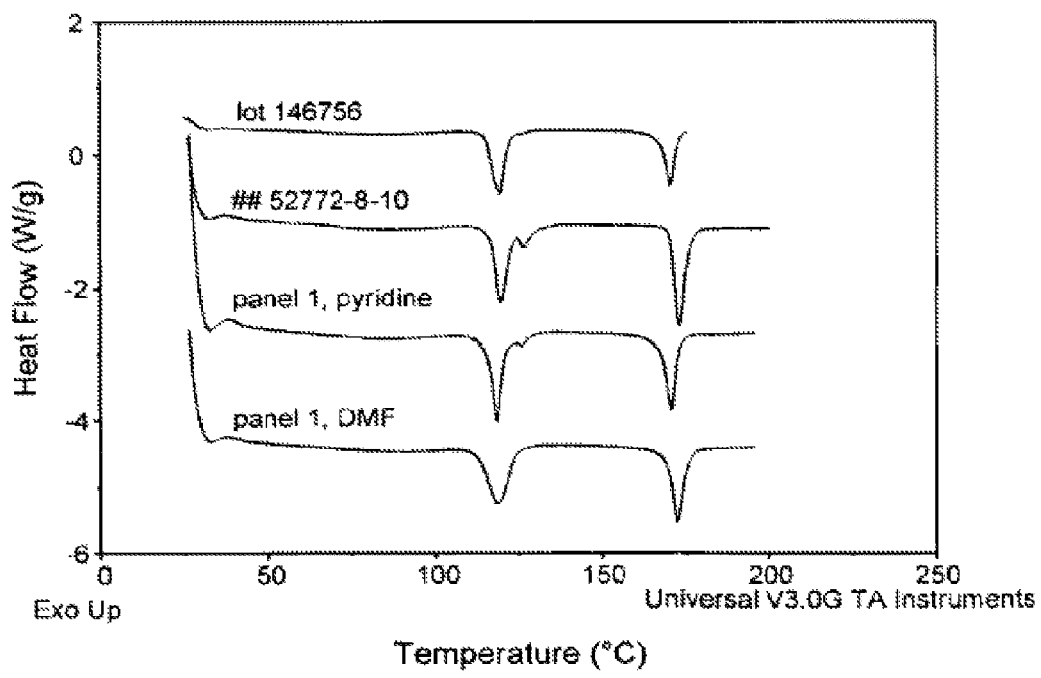
FIG. 11B shows diffraction characteristics of Group A.

This group had approximately 24 members. The characteristic diffraction features of this group are shown in FIG. 11A along with the corresponding thermal features in FIG. 11B. Members of this group were designated as Form A. Samples resulting in Form A originated from different types of polymorph screening experiments (polymorph form control crystallization experiments, crystallization screening experiments, and slurry experiments).

The characteristics of samples of Form A included a nice degree of crystallinity and two major thermal events. The large endothermic event near 115-125° C. signifies the transformation of Form A into a liquid crystal state.

Sometimes the main endothermic signal near 115-125° C. was accompanied by a smaller discernable signal(s) on the low and/or high temperature side. Variable temperature XRD work suggests that Form A reversibly converts to a closely related form that was designated as Form AE.

The second major endothermic event observed in samples of Form A material was attributed to melting at approximately 170° C.

Molecular spectroscopy and TGA of Form A indicate it is an anhydrous, solvent free polymorphic form of the API.

Group B (B1-B4)

The raw chemometric data described as Group B contained approximately 43 members. The variability of diffraction behavior within the group indicated it was composed of four subgroups. These subgroups were designated Groups B1, B2, B3 and B4. In general, samples of the B subgroups exhibited behavior fairly similar to each other and had lower order (crystallinity) than samples of Form A.

Group B1

Figure 12A:
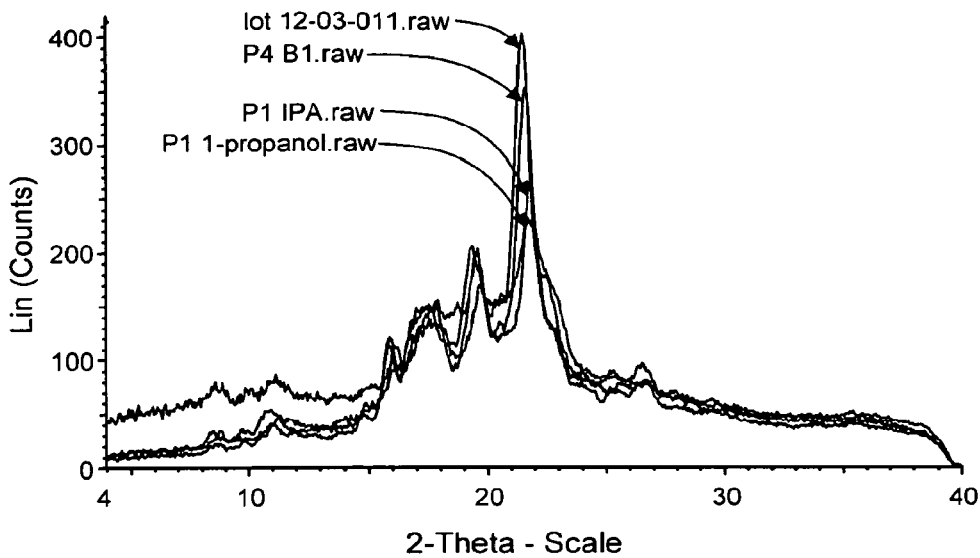
FIG. 12A shows diffraction characteristics of Group B1.
Figure 12B:
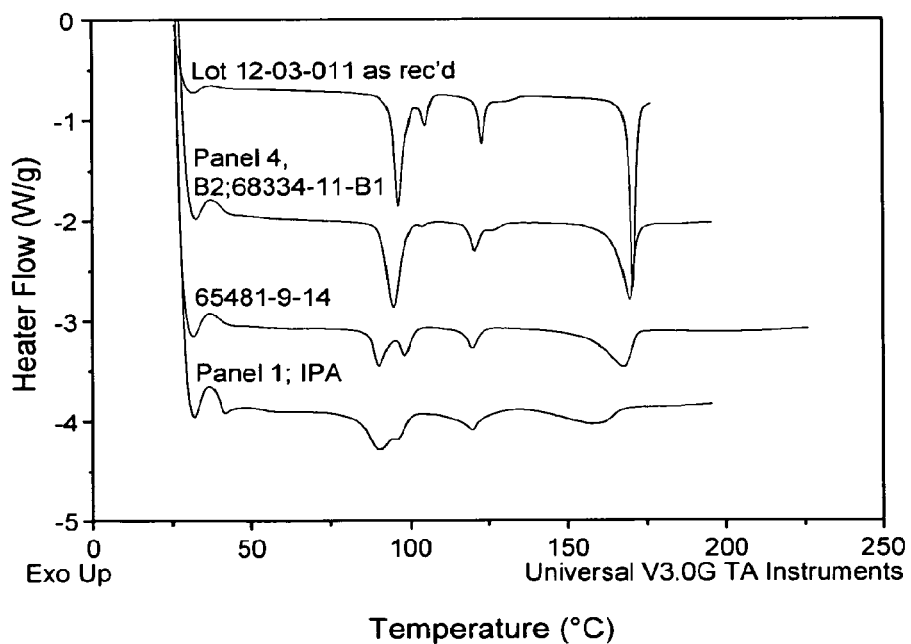
FIG. 12B shows diffraction characteristics of Group B1.

The diffraction and thermal characteristics of Group B1 are shown in FIGS. 12A and 12B, respectively. The characteristic thermal behavior includes three distinct features. The first feature is a pair of endotherms in the 75-110° C. region. The second feature is a small endotherm near 115-125° C. temperature range. The third feature is a melting endotherm near 170° C.

The pair of endotherms near 75-110° C. was attributed to a pair of reversible solid-solid polymorphic transformations that convert Form B1 into Form H. These transitions were followed using variable temperature x-ray diffraction.

The endothermic signal near 115-125° C. was attributed to conversion of Form H into a liquid crystal followed by liquefaction (melting) at 170° C. Note that the variability in the thermograms shown in FIG. 12B may be attributable to some extent to the difference in crystallinity of the samples.

Figure 13A:
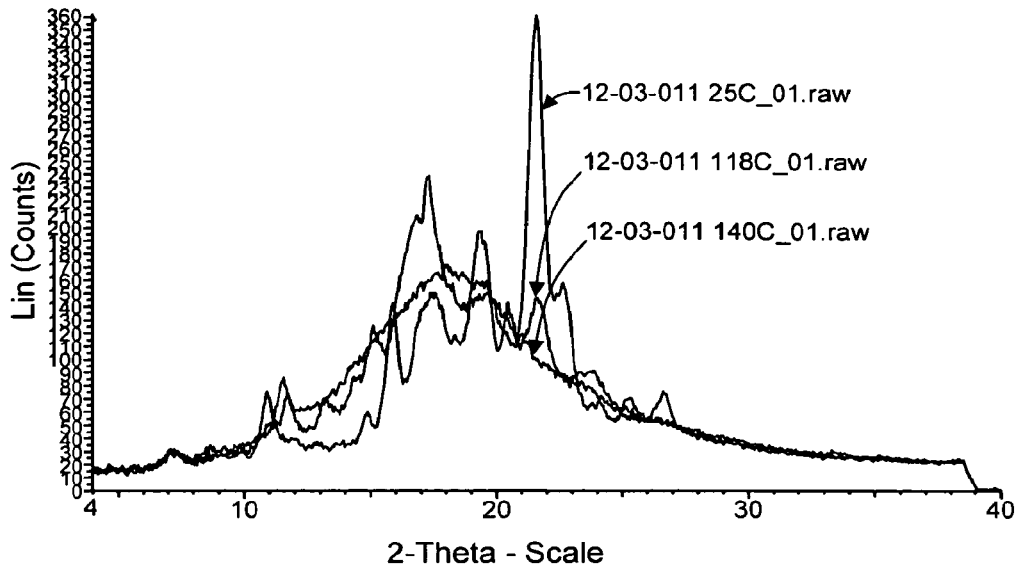
FIG. 13A shows variable temperature XRD characteristics of Form B1 (Lot 12-03-011).
Figure 13B:
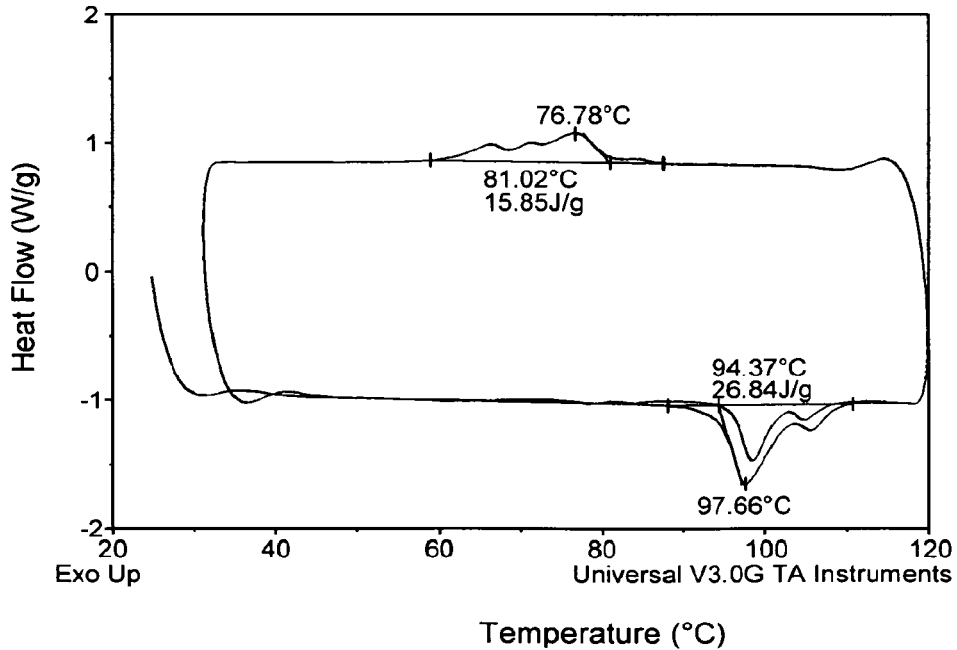
FIG. 13B shows variable thermal characteristics of Form B1 (Lot 12-03-011).

The diffraction pattern of Form H is quite unresolved as is shown in FIG. 13A. The cyclic DSC thermogram in FIG. 13B shows that the transition is reversible as the temperature is raised and lowered.

Molecular spectroscopy and TGA of Form B1 sample indicate it is an anhydrous, solvent free polymorphic form of the API.

Group B2

Figure 14A:
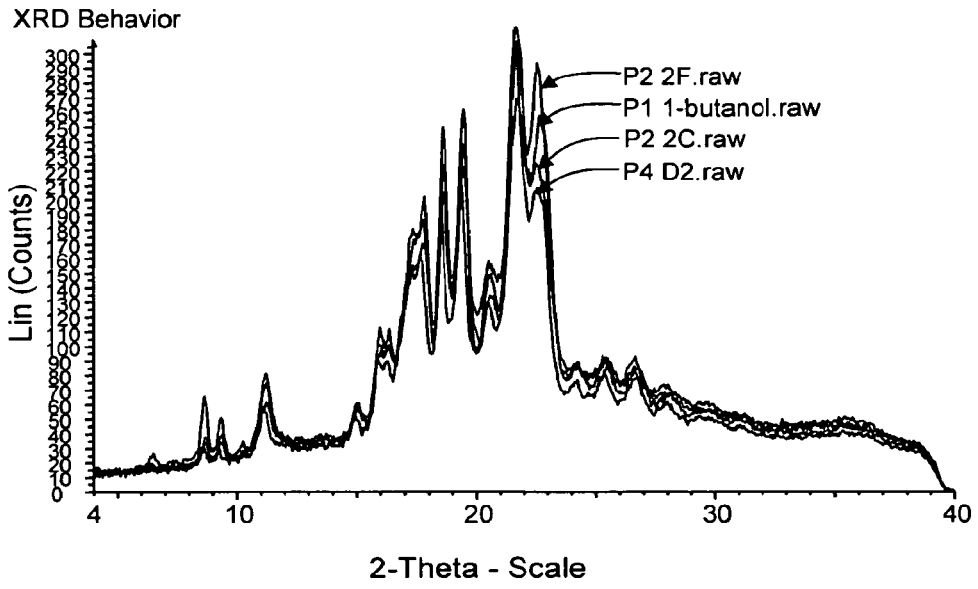
FIG. 14A shows diffraction characteristics of Group B2.
Figure 14B:
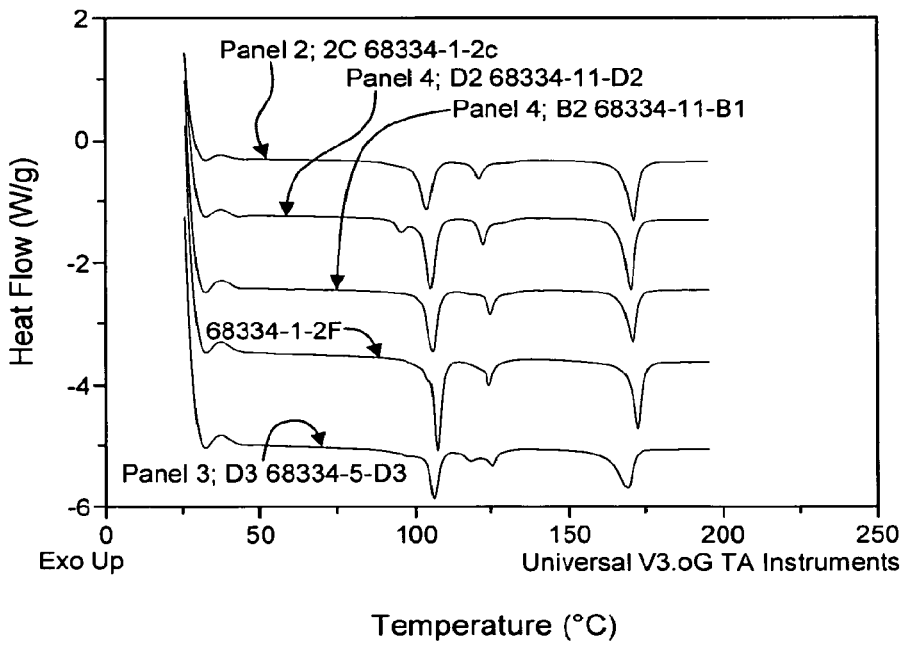
FIG. 14B shows thermal characteristics of Group B2.

Group B2 was the largest of the B subgroups. The diffraction and thermal features of this form are shown in FIGS. 14A and 14B, respectively. This group appeared to have higher crystallinity than group B1 based on the larger number and better resolved diffraction peaks.

Figure 15A:
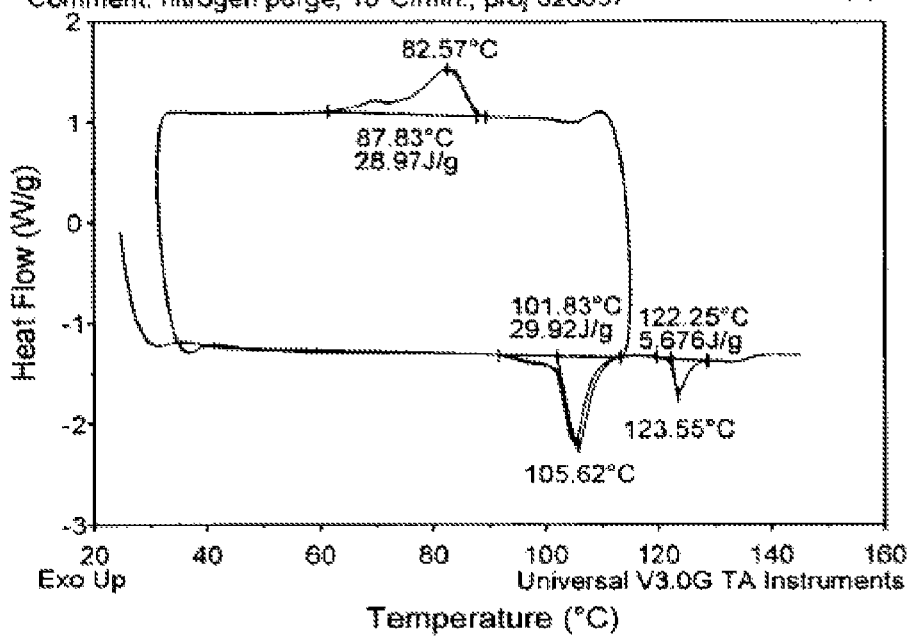
FIG. 15A shows cyclic thermal characteristics of Group B2.
Figure 15B:
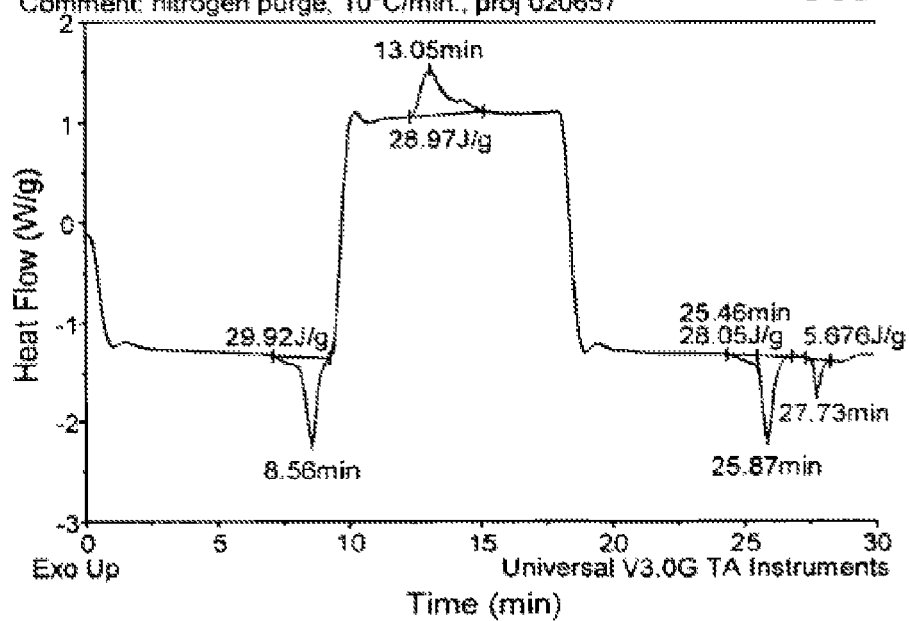
FIG. 15B shows cyclic thermal characteristics of Group B2.

The thermal features of this group include three regions of endothermic features. The first feature is generally a large, convoluted endotherm over the 100-110° C. range. This feature was shown to be reversible (see FIGS. 15A and 15B) using DSC and suggests that Form B2 reversibly converts into a metastable Form designated as Form B2E which transforms into Form H. The second thermal feature is a small endotherm near 125° C. which marks the transformation of Form H into a liquid crystal state. Finally, the liquid crystal state undergoes liquefaction at approximately 170° C.

NMR and TGA of Form B2 samples indicate it is an anhydrous, solvent free polymorphic form of the API.

Group B3

Figure 16A:
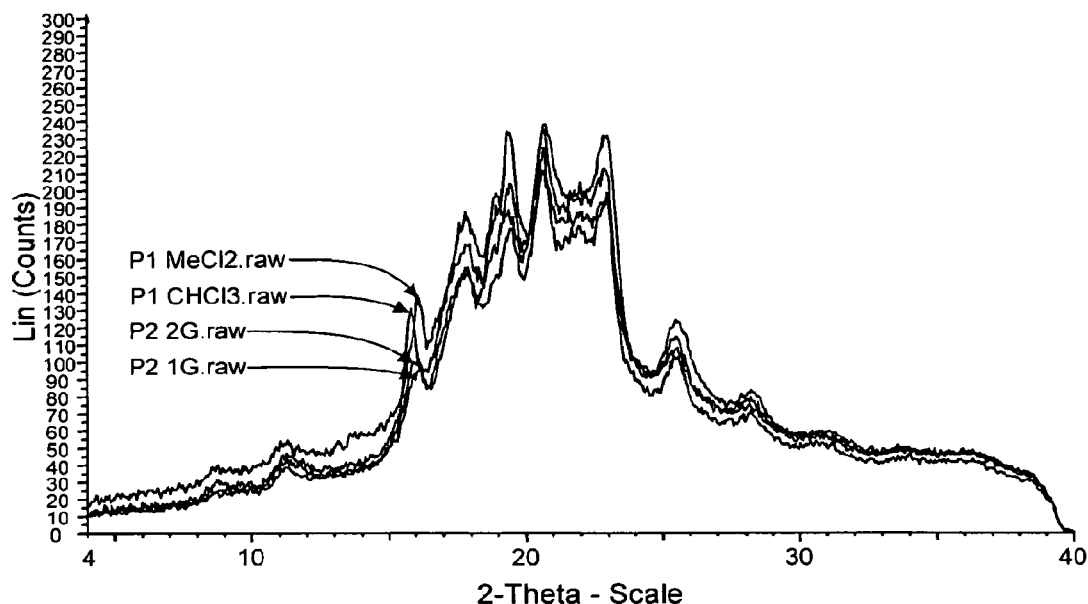
FIG. 16A shows diffraction characteristics of Group B3.
Figure 16B:
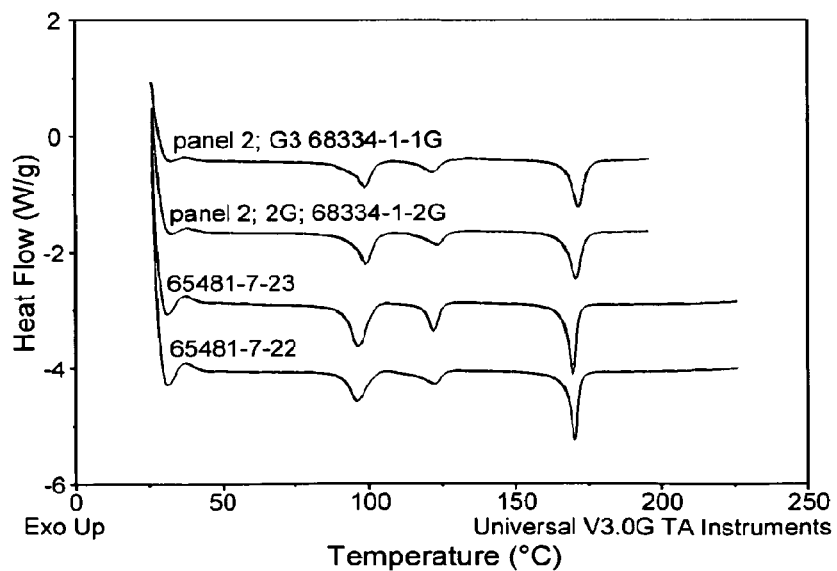
FIG. 16B shows diffraction characteristics of Group B3.

The typical diffraction and thermal behavior of this group are shown in FIGS. 16A and 16B, respectively. The diffraction and thermal characteristics of B3 samples were similar to other group B samples.

Figure 17A:
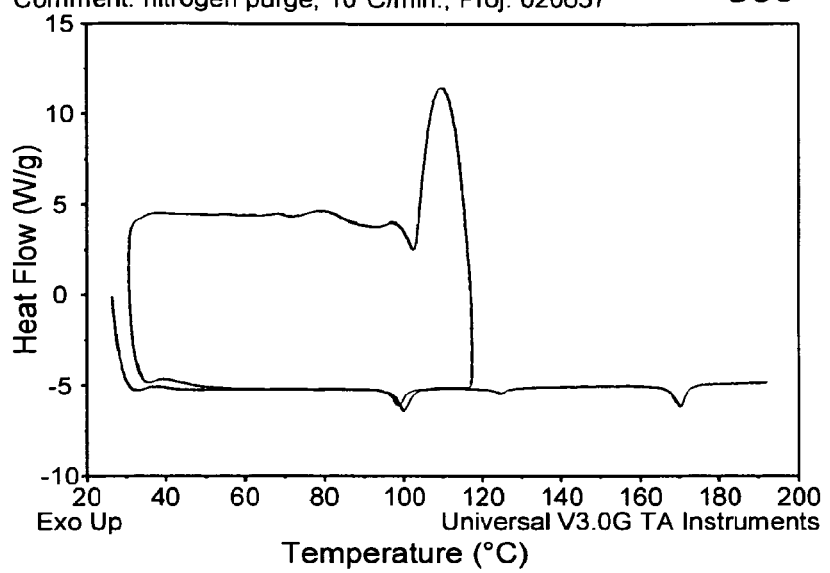
FIG. 17A shows cyclic thermal characteristics of Group B3.
Figure 17B:
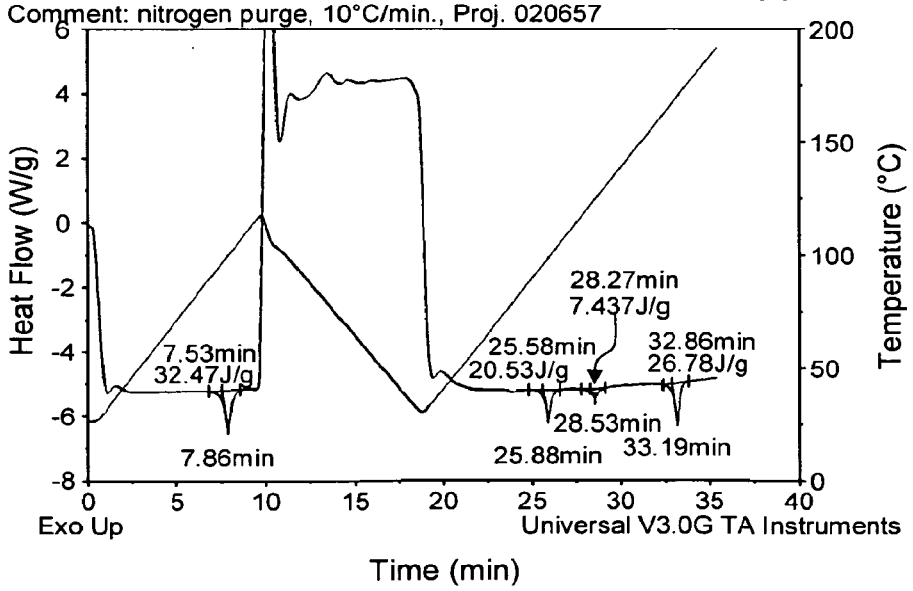
FIG. 17B shows cyclic thermal characteristics of Group B3.

The thermal features of Form B3 are most similar to B1, except B3 samples generally have one distinct endotherm in the 75-110° C. temperature region while Form B1 have two distinct endotherms. The initial endotherm in the 75-110° C. region is believed to represent a polymorphic transformation to Form H. Form H converts to a liquid crystal state at approximately 125° C. and then liquefies at approximately 170° C. FIGS. 17A and 17B shows the cyclic DSC thermogram indicating the conversion of Form B3 to H is reversible as with other Form B/H enantiotropic pairs.

Variable temperature XRD also suggests that Form B3 slowly and reversibly transforms into a closely related structure designated as Form B3E before transforming into Form H.

Molecular spectroscopy and TGA of Form B3 samples indicate it is an anhydrous, solvent free polymorphic form of the API.

Group B4

Figure 18A:
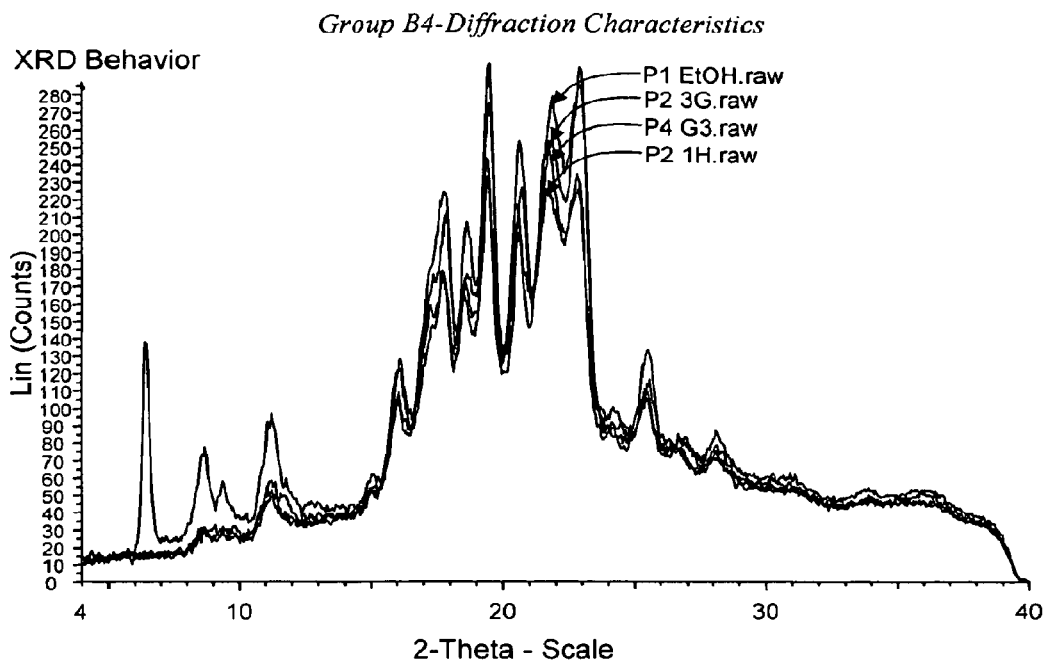
FIG. 18A shows diffraction characteristics of Group B4.
Figure 18B:
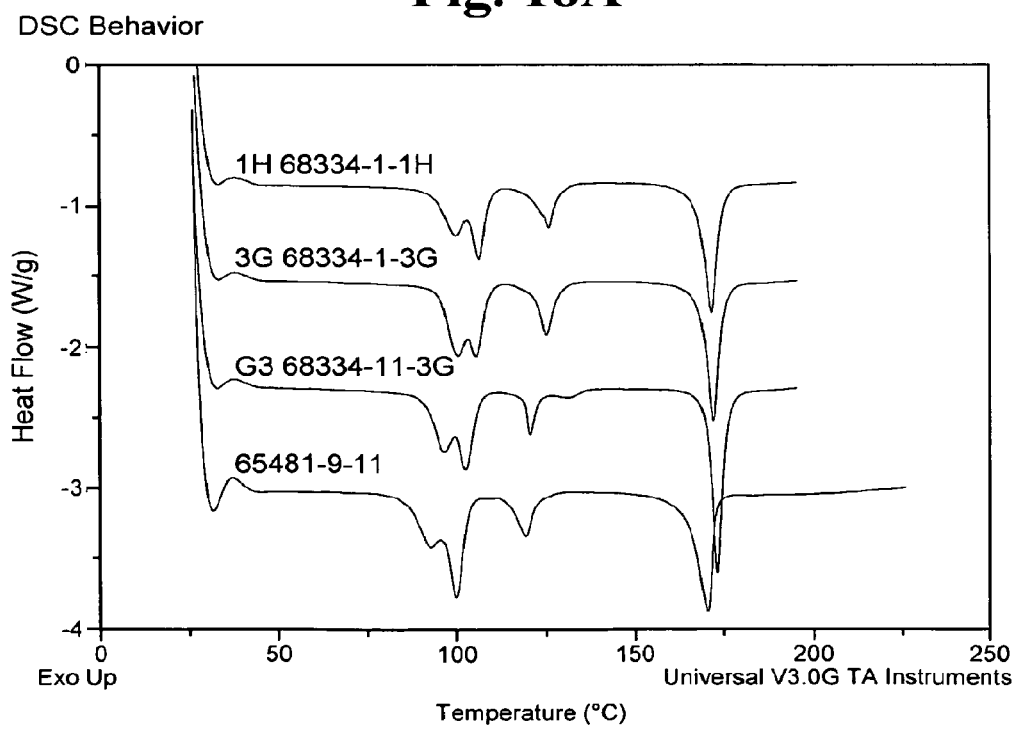
FIG. 18B shows thermal characteristics of Group B4.

The diffraction and thermal behavior are shown in FIGS. 18A and 18B, respectively. The subtle differences in XRD behavior of this group to group B2 include some enhanced and absent reflections at various angles. The thermal characteristics of this group indicate it is similar but different than group B2. Group B4 exhibits two endotherms over the temperature region of approximately 75-110° C. whereas group B2 exhibits only one endotherm.

Figure 19A:
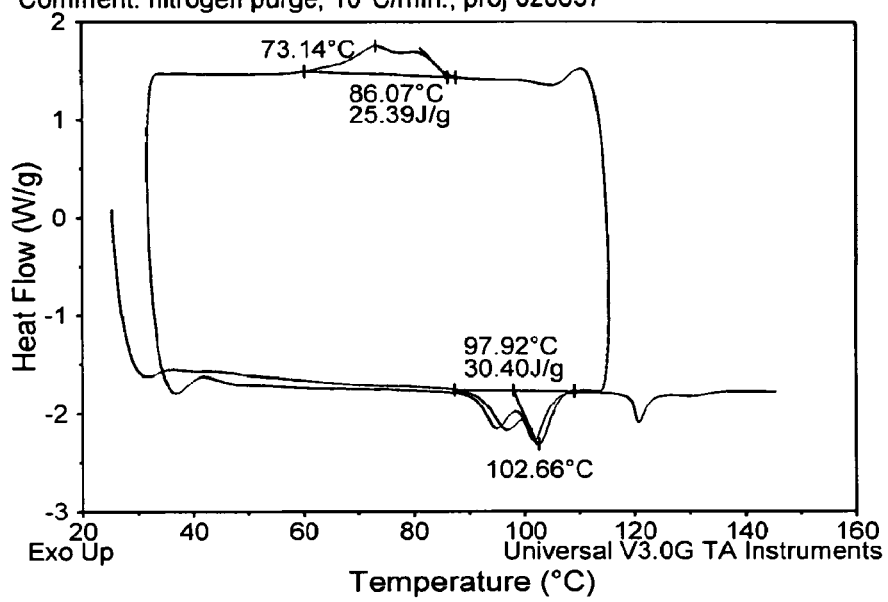
FIG. 19A shows cyclic thermal characteristics of Group B4.
Figure 19B:
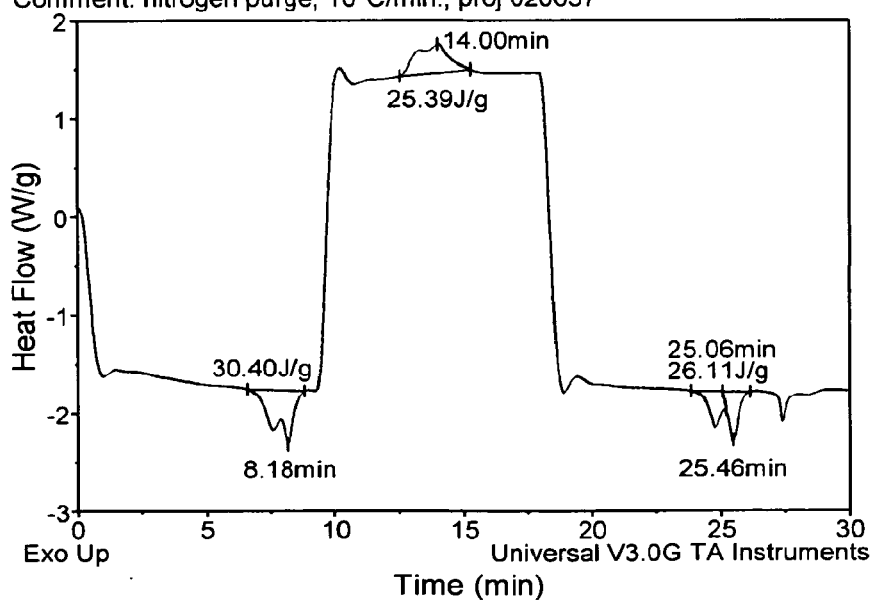
FIG. 19B shows cyclic thermal characteristics of Group B4.

Group B4 reversibly converts (see FIGS. 19A and 19B) to a metastable polymorphic form designated Form H after going through the endothermic region near 75-110° C. This is followed by a smaller endotherm near 125° C. which converts the material into a liquid crystal state. This state remains until the temperature reaches approximately 170° C. when the material liquefies.

Variable temperature XRD was used to study the material as a function of temperature. It appears that Form B4 also undergoes a subtle reversible change to a closely related structure designated as Form B4E before transition to Form H.

Molecular spectroscopy and TGA of Form B4 samples indicate it is an anhydrous, solvent free polymorphic form of the API.

Groups B1-B4

The XRD patterns of all B group members had low crystallinity based on the small number of diffraction peaks and the observation that they were broad and often convoluted. This general feature made it difficult to distinguish and codify the groups B1 through B4 and their corresponding apparent metastable forms (B2E, B3E, B4E) due to a similar type of diffraction appearance. Note that the variable temperature XRD and cyclic DSC indicated that these elevated temperature forms (H, B2E, B3E, B4E) reversibly converted back into B1 through B4 upon cooling. Conversion of Forms H, B2E, B3E, and B4E upon cooling to ambient temperature prevented these forms from being isolated and studied further at ambient temperature.

Group C

Figure 20A:
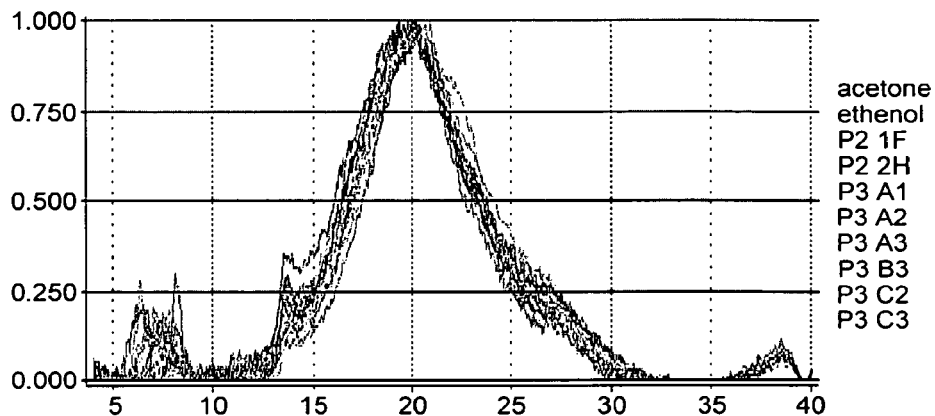
FIG. 20A shows diffraction characteristics of Group C.
Figure 20B:
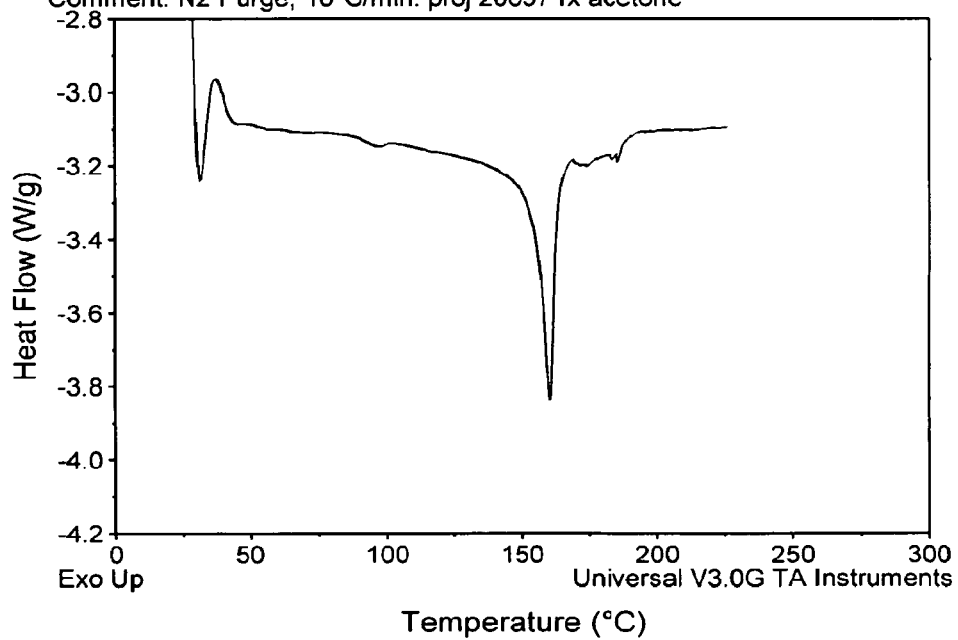
FIG. 20B shows thermal characteristics of Group C.

This group had approximately 23 members. The diffraction and thermal characteristics of this group are shown in FIGS. 20A and 20B, respectively. This group represents samples in a liquid crystal or amorphous state. The x-ray diffractograms only exhibit Bremsstrahlung scattering with a minor diffraction signals at low angles. In general, samples of other forms that were heated until they transformed into a liquid crystal state tended to remain in that state even after cooling to room temperature. Note that there are many types of liquid crystals and the exact nature of the liquid crystal state was not determined, other than it was thermotropic. It is possible that more than one liquid crystal state existed or that the different polymorphic forms identified during the study formed different types of liquid crystal states.

Group H

Group H describes the samples that were only observed by heating samples of group B through their first region of endothermic activity. Each B group sample was observed to transform reversibly into another polymorphic form designated as Form H. The diffraction behavior of Form H at 118° C. is shown by the curve labeled as such in FIG. 13 (the curve labeled 25° C. is Form B1 and the curve labeled 140° C. is liquid crystal).

Energy Relationships

Competitive slurry experiments were performed using mixtures (normally 50:50) of the forms in ethanol and agitating at approximately 25° C. for several days. Noncompetitive slurries were performed by agitating excess solids of one form in ethanol at room temperature. Ethanol was chosen based on its moderate solubility for the polymorphic forms at hand, and the understanding that ethanol did not appear to form solvates with the polymorphic forms.

In both the competitive and noncompetitive slurry experiments, the solids were vacuum filtered and analyzed by XRD. The XRD patterns are used to determine if the undissolved solids had transformed into a different polymorphic form. In one case, a different polymorphic form emerged that was different than either of the two forms initially present. This indicates both original forms were metastable to the final form isolated.

In general, the samples of B polymorphs were readily converted into Form A in the presence of Form A. This indicates Form A is less soluble and more thermodynamically stable than the B polymorphs. Some competitive slurries between two polymorphs of Form B were observed to result in Form A, which further supported this description of the energy relationships.

Non-competitive slurry experiments indicated that the B group polymorphs transformed readily to A even without seeding (or the introduction of Form A). The slurry data are summarized in Table 11.

TABLE 11

Slurry Interconversions of Various Polymorphic Forms

| Starting Form | Final Form |
| --- | --- |
| B1 | A |
| B2 | A |
| B3 | A |
| B4 | A |
| F | A |
| A-B1 | A |
| A-B2 | A |
| B1-B2 | A |

Form C is a liquid crystal state of the material. Being technically a liquid, it was not subject to the slurry experiments.

Form H polymorphs were deemed to be metastable to their corresponding B polymorph counterparts given their reversible endothermic (enantiotropic) relationships. This implies that Form H polymorphs are more soluble and less thermodynamically stable than the B polymorphs. This is consistent with the observation that H polymorphs could not be isolated at ambient temperature due to conversion to the more stable B family polymorphs.

Polymorph Screening Conclusions

The raw diffraction data generated from the polymorph screening experiments (solvent recrystallization, recrystallization from the melt, annealing, non-competitive slurries) were initially categorized into 8 different groups using a chemometric treatment. Analyses of these different groups were used to perform additional experiments (e.g. DSC, TGA, HSM, NMR, etc.) to refine the groups identified by the chemometric treatment. The refinement of these groups resulted in the codification of the polymorphic forms summarized in Table 12.

TABLE 12

Summary of Different Polymorphic Forms

| Form Designation | Description | Comments |
|---|---|---|
| A | Thermodynamically Stable Form | A ↔ AE→LC→molten Target for crystallization and further development |
| B1 | Metastable Polymorph | B1 ↔ H→LC→molten |
| B2 | Metastable Polymorph | B2 ↔ B2E ↔ H→LC→molten |
| B3 | Metastable Polymorph | B3 ↔ B3E ↔ H→LC→molten |
| B4 | Metastable Polymorph | B4 ↔ B4E ↔ H→LC→molten |
| C | Liquid Crystal | Some samples of this group may have been amorphous |
| H | Metastable Polymorph | Enantiotropic Pair of B1-B4 |

All of the different form designations shown in Table 10 were non-solvated, non-hydrated forms. In fact, no apparent solvates were observed during the study. No apparent hydrates were discovered, although formal sorption/hydration studies of each form were not performed. In general, the API was practically insoluble in water and fairly lipophilic suggesting it may not be prone to hydrate formation.

Competitive slurries were used to elucidate the energy relationships between the polymorphic forms capable of being isolated under ambient conditions. The noncompetitive slurry experiments (starting with Form A see Table 10) did not show any polymorphic changes. This, in concert with the non-competitive slurry data, suggests that of the forms discovered during the polymorph screen, Form A appears to be the thermodynamically stable form of the API.

Experimental Methods
Microscopy

A Zeiss Universal microscope configured with a polarized visible light source and polarizable analyzer was used to evaluate the optical properties of the samples. Specimens were typically mounted on a microscope slide with a drop of immersion oil and a cover glass. Magnification was typically 250×. Observations of particle/crystal size and shape were recorded. The presence of birefringence was also noted.

Molecular Spectroscopy—$^1$H-NMR

Samples were prepared by dissolving 1-10 mg in dimethylsulfoxide (DMSO)-d6 with 0.05% (v/v) tetramethylsilane (TMS). Spectra were collected at ambient temperature on a Varian Gemini 300 MHz FT-NMR spectrometer.

Infrared Spectroscopy—FTIR

Infrared spectra were obtained with a Nicolet 510 M-0 Fourier transform infrared spectrometer, equipped with a Harrick Splitpea™ attenuated total reflectance device. Spectra were acquired from 4000-400 cm$^{-1}$ with a resolution of 4 cm$^{-1}$, and 128 scans were collected for each analysis.

Differential Scanning Calometry (DSC)

DSC data were collected on a TA Instruments 2910 DSC. In general, samples in the mass range of 1 to 10 mg were crimped in aluminum sample pans and scanned from 25 to about 175° C. at 10° C./minute using a nitrogen purge at 50 mL/min.

Thermogravimetric Analysis (TGA)

TGA data were collected on a TA Instruments 2950 TGA. In general, samples in the mass range of 5 to 15 mg were placed in an open, pre-tared platinum sample pan and scanned from 25 to about 150° C. at 10° C./minute using a nitrogen purge.

Hot Stage Microscopy (HSM)

A Zeiss Universal microscope configured with a polarized visible light source and a Mettler hot stage accessory was used. Specimens were mounted on a microscope slide with a drop of immersion oil and a cover glass. Magnification was typically 200×. Samples were heated from 25° C. to about 175° C. at 3 or 10° C./minute. Observations of phase change, recrystallization, evolution of bubbles, etc. were recorded.

Powder Flow

Powder flow characteristics were compared using the Carr Index. By subjecting a powder to mechanical forces, resistance to powder flow can be observed. The increase in bulk density (compressibility) of a powder subjected to tapping can be used to determine the Carr index. A summary of Carr indices and qualitative flow properties are summarized below in Table 13.

TABLE 13

| Compressibility (Carr Index) | Flowability |
|---|---|
| 5-12 | Free flowing |
| 12-16 | Good flow |
| 18-21 | Fair |
| 23-35 | Poor |
| 33-38 | Very Poor |
| >40 | Extremely Poor |

Batches were sieved to <1000 microns before testing. This was necessary to remove any clumps in the samples.

High Performance Liquid Chromatography (HPLC)

LC data were collected using a Perkin Elmer HPLC with an LC-410 pump, LC-235 diode array detector, and 200 series autosampler. The HPLC was equipped with a peltier controller sample tray and a column heater. Data were collected via a validated client-server LIMS.

The HPLC method employed was as follows: Column: Phenomenex INERSIL ODS-2, 250×4.6 mm, 5 micron particle size; Mobile Phase: 0.2% perchloric acid in 62:38 Acetonitrile:water/Acetonitrile; Gradient: 0 to 95% over 25 minutes; Flow Rate: 1.5 mL/min; Detection: 254 nm, suggests that by extending the timing of the crystallization (to include an overnight stir of the suspension after crystallization), an impurity (guanine stearate alcohol) builds to about 0.9 area %, from an original starting level of about 0.3 area %. By following the times and temperatures quoted, the build of the impurity is limited to 0.6 area %, which is currently considered acceptable.

Liquid Chromatography Mass Spectrometry (LCMS)

Data was collected using an Agilent 1100 LC/MS system consisting of the following components: a G1367A wellplate sampler, a G1316A column heating compartment, a G1315A diode array detector, a G1322A vacuum degasser, a G1312A binary pump, and a G1946C mass spec detector (electrospray single-quad).

The LC conditions were chosen based on the HPLC method previously described. The main modification to the method was to use formic acid rather than perchloric acid. Samples were analyzed using electrospray by UV diode array and positive ion mode MS.

X-Ray Powder Diffraction (XRD)

X-ray powder diffraction patterns were obtained using a Bruker D8 Discovery diffractometer equipped with an XYZ stage, laser video microscope for positioning, and a two dimensional HiStar area Detector. Collection times were nominally 60 seconds. A Cu Kα radiation 1.5406 angstrom source operating at 40 kV and 40 mA was used to irradiate samples. The X-ray optics consists of a Gobel mirror coupled with a pinhole collimator of 0.5 mm. Theta-theta continuous scans were employed with a sample-detector distance of 15 cm, which gives an effective 2θ range of 4-40°. Samples were mounted in low background quartz plates. A variable temperature hot stage was used to manipulate sample temperature for some experiments.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. Crystalline valomaciclovir having characteristic absorption peaks at 2θ angles of 22.9°±0.2°, 18.6°±0.2°, 19.5°±0.2°, 24.3°±0.2°, 20.8°±0.2°, 21.8°±0.2°, 27.0°±0.2°, 14.7°±0.2°, 15.5°±0.2°, 25.5°±0.2°, and 29.9°±0.2° with Cu Kα radiation in a X-ray powder diffractogram.

2. A pharmaceutical composition comprising crystalline valomaciclovir according to claim 1 and a pharmaceutically acceptable excipient or diluent.

3. The crystalline valomaciclovir of claim 1 which is at least 90% crystallographically pure.

4. The crystalline valomaciclovir of claim 1 which is at least 95% crystallographically pure.

5. The crystalline valomaciclovir of claim 1 which is at least 99% crystallographically pure.

6. A process of preparing crystalline valomaciclovir according to claim 1, comprising the steps of:
dissolving valomaciclovir in a lower alkanol solvent or a mixed solvent of lower alkanols by heating to a temperature to dissolve the valomaciclovir in the lower alkanol solvent or the mixed solvent of lower alkanols; cooling the solution with stirring;
collecting the crystalline valomaciclovir.

7. The process of claim 6, wherein the lower alkanol solvent is ethanol.

8. The process of claim 6, wherein the mixed solvent of lower alkanols is a mixture of 95:5 (v/v) ethanol/2-propanol.

9. The process of claim 6, wherein the temperature is from 65° C. to 74° C.

10. The process of claim 9, wherein the temperature is from 68° C. to 72° C.

11. The process of claim 6, wherein the cooling is at a rate of from 5° C. to 15° C. per hour.

12. The process of claim 11, wherein the cooling is at a rate of from 8° C. to 12° C. per hour.

13. A method of treating a viral infection in a subject comprising administering to the subject in need thereof a therapeutically effective amount of the crystalline compound of claim 1, wherein the viral infection is a varicella zoster virus infection.

* * * * *